(12) United States Patent
Yoneyama

(10) Patent No.: US 11,911,409 B2
(45) Date of Patent: Feb. 27, 2024

(54) PHARMACEUTICAL COMPOSITION FOR TREATMENT AND PREVENTION OF CHRONIC DISEASE

(71) Applicant: STELIC INSTITUTE & CO., INC., Tokyo (JP)

(72) Inventor: Hiroyuki Yoneyama, Minato-ku (JP)

(73) Assignee: STELIC INSTITUTE & CO., INC., Tokyo (JP)

( * ) Notice: Subject to any disclaimer, the term of this patent is extended or adjusted under 35 U.S.C. 154(b) by 35 days.

(21) Appl. No.: 17/506,012

(22) Filed: Oct. 20, 2021

(65) Prior Publication Data

US 2022/0323481 A1     Oct. 13, 2022

Related U.S. Application Data

(63) Continuation of application No. 16/467,410, filed as application No. PCT/JP2017/044090 on Dec. 7, 2017, now abandoned.

(60) Provisional application No. 62/431,014, filed on Dec. 7, 2016.

(51) Int. Cl.

| | | |
|---|---|---|
| *C07H 21/04* | (2006.01) | |
| *A61K 31/7105* | (2006.01) | |
| *A61K 31/711* | (2006.01) | |
| *A61K 31/713* | (2006.01) | |
| *A61K 38/13* | (2006.01) | |
| *A61P 1/00* | (2006.01) | |
| *A61P 37/06* | (2006.01) | |
| *C07K 16/28* | (2006.01) | |
| *C12N 15/113* | (2010.01) | |
| *A61K 45/06* | (2006.01) | |
| *C12N 15/63* | (2006.01) | |

(52) U.S. Cl.
CPC ........ *A61K 31/7105* (2013.01); *A61K 31/711* (2013.01); *A61K 31/713* (2013.01); *A61K 38/13* (2013.01); *A61P 1/00* (2018.01); *A61P 37/06* (2018.01); *C07K 16/2839* (2013.01); *C12N 15/113* (2013.01); *A61K 45/06* (2013.01); *C12N 15/63* (2013.01); *C12N 2310/14* (2013.01)

(58) Field of Classification Search
CPC .......................... C12N 15/113; C12N 2310/14
See application file for complete search history.

(56) References Cited

U.S. PATENT DOCUMENTS

| | | |
|---|---|---|
| 2010/0266531 A1 | 10/2010 | Hsieh et al. |
| 2013/0172235 A1 | 7/2013 | Kjaer et al. |
| 2014/0120084 A1 | 5/2014 | Anand et al. |
| 2015/0337313 A1 | 11/2015 | Yoneyama et al. |
| 2016/0095921 A1 | 4/2016 | Ebsworth et al. |
| 2017/0327584 A1 | 11/2017 | Lasch |

FOREIGN PATENT DOCUMENTS

| | | | |
|---|---|---|---|
| JP | 2012-519708 A | 8/2012 | |
| JP | 2014-515018 A | 6/2014 | |
| JP | 2014-523906 A | 9/2014 | |
| WO | WO 2009/004995 A1 | 1/2009 | |
| WO | WO 2009/084232 A1 | 7/2009 | |
| WO | WO 2010/102251 A2 | 9/2010 | |
| WO | WO 2012/135589 A1 | 10/2012 | |
| WO | WO 2013/007596 A2 | 1/2013 | |
| WO | WO 2014/013535 A1 | 1/2014 | |
| WO | WO 2016/057424 A1 | 4/2016 | |
| WO | WO 2016/086147 A1 | 6/2016 | |
| WO | WO 2017/078054 A1 | 5/2017 | |
| WO | WO 2018/183934 A1 * | 10/2018 | ........... C12N 15/113 |

OTHER PUBLICATIONS

International Search Report dated Mar. 6, 2018 in PCT/JP2017/044090 filed on Dec. 7, 2017.
Watanabe, K. et al., "Small interfering RNA therapy against carbohydrate sulfotransferase 15 inhibits cardiac remodeling in rats with dilated cardiomyopathy", Cellular Signalling, Jul. 2015, vol. 27, No. 7, 8 pages.
Suzuki, K. et al., "Pivotal Role of Carbohydrate Sulfotransferase 15 in Fibrosis and Mucosal Healing in Mouse Colitis", PLOS One, Jul. 13, 2016, vol. 11, No. 7, pp. 1-17.
Patnode, M. L. et al., "KSGal6ST generates galactose-6-O-sulfate in high endothelial venules but does not contribute to L-selectin-dependent lymphocyte homing", Glycobiology, vol. 23, No. 3, 2013, pp. 381-394.
Kiryu, H. et al., "A detailed investigation of accessibilities around target sites of siRNAs and miRNAs", Bioinformatics, vol. 27, No. 13, 2011, pp. 1788-1797.
Suzuki, K. et al., "Endoscopic Submucosal Injection of a Synthesized Anti-CHST15 dsRNA for Sulfated Glycosaminoglycan is a Safe and Beneficial Treatment for Patients With Crohn's Disease Who Do Not Respond Sufficiently to the Conventional Treatment", Gastroenterology, Su1078, 2014, 1 page (Abstract).
Extended European Search Report dated Jun. 18, 2020 in Patent Application No. 17879130.7, 10 pages.
Mark Löwenberg, et al. "Next-Generation Therapeutics for IBD" Current Gastroenterology Reports, Current Science, vol. 17, No. 21, XP035506827, Jun. 2, 2015, pp. 1-8.

(Continued)

*Primary Examiner* — Amy H Bowman
(74) *Attorney, Agent, or Firm* — Oblon, McClelland, Maier & Neustadt, L.L.P.

(57) ABSTRACT

An object of the present invention is to develop a novel treatment method for chronic diseases for which conventional treatment methods are either ineffective or for which efficacy is low. The present invention provides a pharmaceutical composition for the treatment and/or prevention of an inflammatory chronic disease that is used in combination with a biological preparation that inhibits leukocyte tissue invasion. The pharmaceutical composition of the present invention contains as an active ingredient thereof siRNA suppressing the expression of CHST15 gene that contains a structure formed by the hybridization of RNA containing the base sequence represented by SEQ ID NO: 1 with RNA complementary thereto.

10 Claims, 8 Drawing Sheets

Specification includes a Sequence Listing.

(56) References Cited

OTHER PUBLICATIONS

Atreya et al., Abstracts of the 12th Congress of ECCO—European Crohn's and Colitis Organization, "DOP073. Submucosal injection of the oligonucleotide STNM01 is able to induce clinical remission, mucosal healing and histological response in left-sided ulcerative colitis patients with moderate-to-severe disease", p. S69, Jan. 26, 2017.

Allex et al., "Report of the ECCO pathogenesis workshop on anti-TNF therapy failures in inflammatory bowel diseases: Definitions, frequency and pharmacological aspects", Journal of Crohn's and Colitis (2010) 4, 355-366.

Neurath, "New targets for mucosal healing and therapy in inflammatory bowel diseases", Micosal Immunology, Review, vol. 7 No. 1, Nature Publishing Group, published on line Oct. 2, 2013. 14 pages.

\* cited by examiner

Primary Evaluation Parameter: Induction of Mucosal Healing

PHARMACEUTICAL COMPOSITION FOR TREATMENT AND PREVENTION OF CHRONIC DISEASE

TECHNICAL FIELD

The present invention relates to a pharmaceutical composition comprising as active ingredients thereof siRNA and a DNA vector capable of expressing that siRNA, and more particularly, relates to inhibition of expression of human CHST15, a pharmaceutical composition comprising as active ingredients thereof siRNA and a DNA vector capable of expressing that siRNA, the use thereof, and an administration method.

BACKGROUND ART

Many chronic diseases are autoimmune diseases that are associated with chronic inflammation. In recent years, attention has focused on the invasion of tissue by leukocytes involved in inflammation as a novel treatment target for these chronic diseases. The invasion of inflammatory tissue by leukocytes circulating in the blood consists of the four stages indicated below. Namely, (1) decrease in leukocyte flow rate due to a first interaction between vascular endothelial cells and leukocytes in the vicinity of the inflammation site (rolling), (2) activation of rolling leukocytes, (3) strong adhesion of the aforementioned activated leukocytes to the aforementioned vascular endothelial cells due to a second interaction in the vicinity of the inflammation site, and (4) final migratory invasion of the aforementioned activated leukocytes into tissue by slipping through blood vessels by passing between vascular endothelial cells. Among these stages, bonding between L-selectin on the surface of the leukocytes and the end of a 6-sulfosiallyl Lewis X-type sugar chain of L-selectin ligand present on the surface of vascular endothelial cells is known to be involved in the first stage rolling. N-acetylglucosamine-6-sulfotransferase is known to be involved as the enzyme involved in inflammation site-specific synthesis of this 6-sulfosiallyl Lewis X-type sugar chain, and N-acetylglucosamine-6-sulfotransferase encoded by human CHST2 and CHST4 genes has conventionally been thought to be involved in invasion of inflammatory tissue by leukocytes circulating in the blood. However, based on research conducted on knockout mice, although circulating leukocytes invade inflammatory tissue even in mice lacking both CHST2 and CHST4 genes, the reason for this has not been clearly determined (Non-Patent Document 1).

The inventors of the present invention reported therapeutic effects, including inhibition of ulceration, inflammation and fibrosis, using siRNA expressing sulfotransferase CHST15 that is different from CHST2 and CHST4 (Patent Documents 1 to 3 and Non-Patent Documents 1 and 2). In particular, a phase IIa clinical trial was recently conducted on human Crohn's disease patients, and it was demonstrated that when the aforementioned siRNA was administered by submucosal administration into the large intestine of these patients, healing of the mucosa or healing of ulceration was able to be achieved endoscopically.

During the course thereof, since siRNA therapy using CHST15 yields superior treatment results in comparison with conventional biological preparation therapy for Crohn's disease, it was found that siRNA of CHST15 inhibits the first stage of invasion of inflammatory tissue by circulating leukocytes, thereby leading to completion of the present invention.

PRIOR ART DOCUMENTS

Patent Documents

[Patent Document 1] International Publication No. WO 2009/004995
[Patent Document 2] International Publication No. WO 2009/084232
[Patent Document 3] International Publication No. WO 2014/013535

Non-Patent Documents

[Non-Patent Document 1] Patnode, M. L., et al., Glycobiology, 23: 381-394 (2013)
[Non-Patent Document 2] Kiryu, H., et al., Bioinformatics, 27: 1788-1797 (2011)
[Non-Patent Document 3] Suzuki, K., et al., Sul078 Gastroenterology 204: (suppl.)

DISCLOSURE OF THE INVENTION

Problems to be Solved by the Invention

It is necessary to develop a novel treatment method for chronic disease for which conventional treatment methods are either ineffective or for which efficacy is low.

Means for Solving the Problems

Since siRNA that inhibits expression of CHST15 inhibits expression of 6-sulfosiallyl Lewis X of the L-selectin ligand of vascular endothelial cells at an inflammation site, a novel technology for chronic disease was developed using the aforementioned siRNA that can be used in combination with conventional therapy.

The present invention provides a pharmaceutical composition for the treatment and/or prevention of an inflammatory chronic disease that is used in combination with a biological preparation inhibiting leukocyte tissue invasion and/or a biological preparation inhibiting inflammatory cytokines. The pharmaceutical composition of the present invention contains as active ingredients thereof:

(i) siRNA suppressing the expression of CHST15 gene that contains a structure formed by the hybridization of RNA containing the base sequence represented by SEQ ID NO: 1 with RNA containing the base sequence represented by SEQ ID NO: 2 complementary thereto,
(ii) the siRNA of (i) having a structure in which one or a plurality of nucleic acids overhang from the end thereof, or
(iii) a DNA vector capable of expressing the siRNA of (i) or (ii).

In the pharmaceutical composition of the present invention, the siRNA of (i) may have a structure formed by the hybridization of RNA composed of the base sequence represented by SEQ ID NO: 1 with RNA composed of the base sequence represented by SEQ ID NO: 2 complementary thereto.

In the pharmaceutical composition of the present invention, the siRNA of (ii) may have a structure formed by the hybridization of RNA composed of the base sequence represented by SEQ ID NO: 3 with RNA composed of the base sequence represented by SEQ ID NO: 4 complementary thereto.

In the pharmaceutical composition of the present invention, the biological preparation inhibiting leukocyte tissue invasion may inhibit the function of at least one molecule selected from the group consisting of integrin and/or chemokine receptor on the surface of leukocytes circulating in the blood and adhesion molecules on the surface of vascular endothelial cells.

In the pharmaceutical composition of the present invention, the biological preparation inhibiting leukocyte tissue invasion may be at least one member selected from the group consisting of Etrolizumab, Vedolizumab, Natalizumab, PF-00547659 and Vercirnon.

In the pharmaceutical composition of the present invention, the biological preparation inhibiting inflammatory cytokines may inhibit the function of at least one molecule selected from the group consisting of TNF-α, IL-17 and IL-23.

The pharmaceutical composition of the present invention may further use in combination at least one member selected from the group consisting of a 5-aminosalicyclic acid preparation, steroid preparation, thiopurine preparation, and immunosuppressants including tacrolimus and cyclosporine.

The present invention provides a pharmaceutical composition for the treatment and/or prevention of chronic disease in which 6-sulfosiallyl Lewis X of L-selectin ligand is expressed on the surface of the vascular endothelial cells of a patient. The pharmaceutical composition of the present invention contains as active ingredients thereof:
  (i) siRNA suppressing the expression of CHST15 gene that contains a structure formed by the hybridization of RNA containing the base sequence represented by SEQ ID NO: 1 with RNA containing the base sequence represented by SEQ ID NO: 2 complementary thereto,
  (ii) the siRNA of (i) having a structure in which one or a plurality of nucleic acids overhang from the end thereof, or
  (iii) a DNA vector capable of expressing the siRNA of (i) or (ii).

In the pharmaceutical composition of the present invention, the siRNA of (i) may have a structure formed by the hybridization of RNA composed of the base sequence represented by SEQ ID NO: 1 with RNA composed of the base sequence represented by SEQ ID NO: 2 complementary thereto.

In the pharmaceutical composition of the present invention, the siRNA of (ii) may have a structure formed by the hybridization of RNA composed of the base sequence represented by SEQ ID NO: 3 with RNA composed of the base sequence represented by SEQ ID NO: 4 complementary thereto.

In the pharmaceutical composition of the present invention, the chronic disease may be an autoimmune disease.

In the pharmaceutical composition of the present invention, the autoimmune disease may be at least one disease selected from the group consisting of inflammatory colitis, Crohn's disease, ulcerative colitis, autoimmune pancreatitis, chronic rheumatoid arthritis, bronchial asthma, chronic interstitial pneumonia, Grave's disease, Hashimoto's thyroiditis, chronic thyroiditis and atopic dermatitis.

The pharmaceutical composition of the present invention may be administered systemically or locally.

In the pharmaceutical composition of the present invention, the autoimmune disease may be selected from the group consisting of inflammatory colitis, Crohn's disease and ulcerative colitis, and the local administration may be submucosal administration into the intestine of a patient.

In the pharmaceutical composition of the present invention, the systemic administration may be oral administration and/or intravenous injection.

In the pharmaceutical composition of the present invention, a complex may be administered orally that contains N-acetylated chitosan and an active ingredient in the form of:
  (i) siRNA suppressing expression of CHST15 gene that contains a structure obtained as a result of hybridization of RNA containing the base sequence represented by SEQ ID NO: 1 with RNA containing the base sequence represented by SEQ ID NO: 2 complementary thereto, or
  (ii) the siRNA of (i) having a structure in which one or a plurality of nucleic acids overhang from the end thereof.

The present invention provides a method for treating and/or preventing an inflammatory chronic disease that includes the combined use of the pharmaceutical composition of the present invention with a biological preparation inhibiting leukocyte tissue invasion and/or a biological preparation inhibiting inflammatory cytokines. Here, the pharmaceutical composition of the present invention contains as active ingredients thereof:
  (i) siRNA suppressing the expression of CHST15 gene that contains a structure formed by the hybridization of RNA containing the base sequence represented by SEQ ID NO: 1 with RNA containing the base sequence represented by SEQ ID NO: 2 complementary thereto,
  (ii) the siRNA of (i) having a structure in which one or a plurality of nucleic acids overhang from the end thereof, or
  (iii) a DNA vector capable of expressing the siRNA of (i) or (ii).

In the method for treating and/or preventing an inflammatory chronic disease of the present invention, the siRNA of (i) may have a structure formed by the hybridization of RNA composed of the base sequence represented by SEQ ID NO: 1 with RNA composed of the base sequence represented by SEQ ID NO: 2 complementary thereto.

In the method for treating and/or preventing an inflammatory chronic disease of the present invention, the siRNA of (ii) may have a structure formed by the hybridization of RNA composed of the base sequence represented by SEQ ID NO: 3 with RNA composed of the base sequence represented by SEQ ID NO: 4 complementary thereto.

In the method for treating and/or preventing an inflammatory chronic disease of the present invention, the biological preparation inhibiting leukocyte tissue invasion may inhibit the function of at least one molecule selected from the group consisting of integrin and/or chemokine receptor on the surface of leukocytes circulating in the blood and adhesion molecules on the surface of vascular endothelial cells.

In the method for treating and/or preventing an inflammatory chronic disease of the present invention, the biological preparation inhibiting leukocyte tissue invasion may be at least one member selected from the group consisting of Etrolizumab, Vedolizumab, Natalizumab, PF-00547659 and Vercirnon.

In the method for treating and/or preventing an inflammatory chronic disease of the present invention, the biological preparation inhibiting inflammatory cytokines may inhibit the function of at least one molecule selected from the group consisting of TNF-α, IL-17 and IL-23.

The method for treating and/or preventing an inflammatory chronic disease of the present invention may further use in combination at least one anti-inflammatory agent, immunomodulator or immunosuppressant selected from the group consisting of a 5-aminosalicyclic acid preparation, steroid preparation, thiopurine preparation and tacrolimus.

All publications mentioned in the present description are incorporated in the present description in their entirety by reference.

BEST MODE FOR CARRYING OUT THE INVENTION

Figure 1:
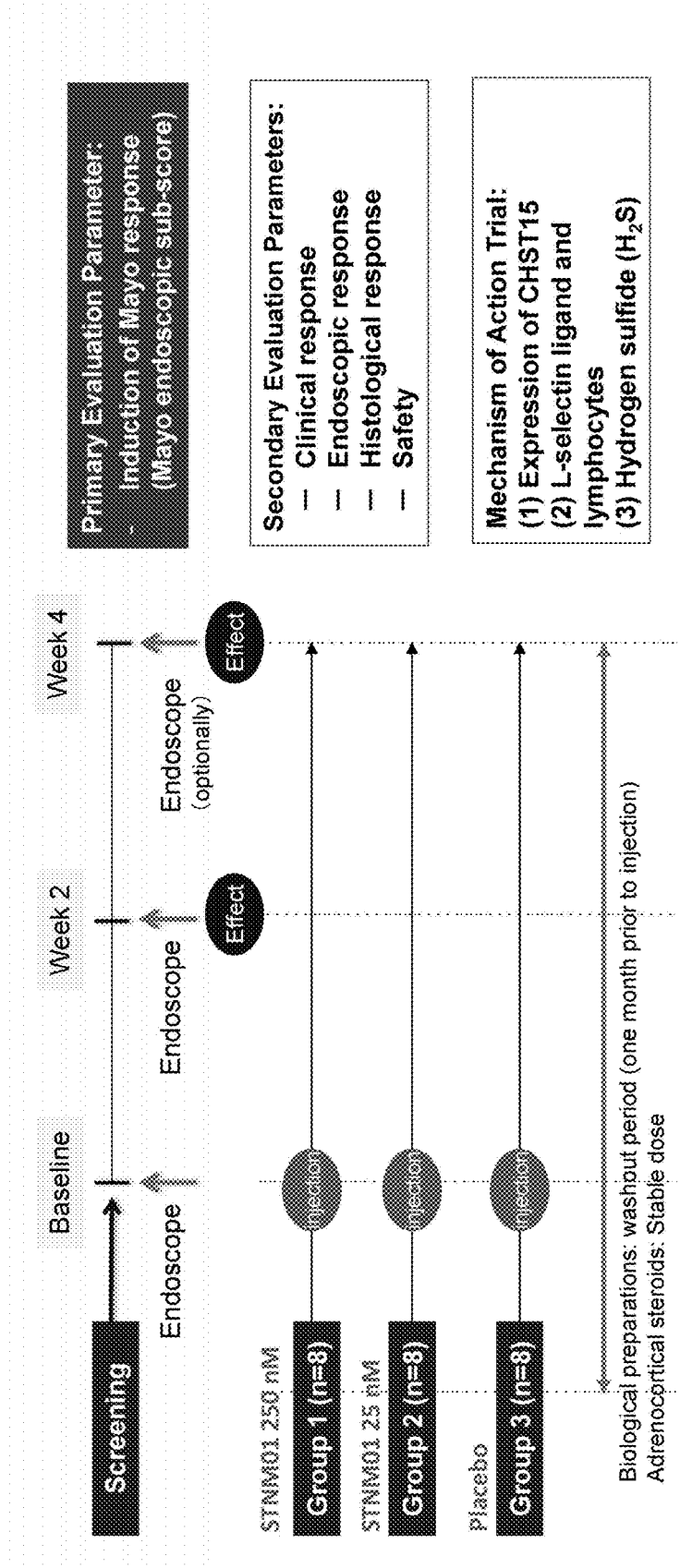
FIG. 1 is a schematic diagram of the design of a phase IIa clinical trial of the pharmaceutical composition of the present invention against ulcerative colitis.

In the present invention, an RNAi molecule is able to suppress expression of CHST15 gene. In the present description, an "RNAi molecule" refers to an RNA molecule capable of inducing RNA interference (RNAi) in the body and suppressing (silencing) the expression of a target gene (CHST15 in the present invention) via, for example, degradation of the transcription product thereof (Fire, A., et al., Nature 391, 806-811 (1998)). Specific examples of RNAi molecules include siRNA and shRNA. "siRNA" refers to double-stranded RNA formed by the hybridization of an antisense strand containing a sequence complementary to a portion of the mRNA sequence of a target gene with a sense strand containing a sequence complementary to the antisense strand (sequence homologous to a portion of the sequence of a target gene). "shRNA" refers to single-stranded RNA in which the sense strand and antisense strand of the aforementioned siRNA are linked by a short spacer sequence having a suitable sequence. In other words, shRNA forms a stem-loop hairpin structure throughout the molecule by forming a stem structure as a result of the sense region and antisense region mutually undergoing base pairing within a single molecule to form a stem structure while the aforementioned spacer sequence simultaneously forms a loop structure.

In the present description, suppression of the expression of a target gene refers not only to suppressing by 100%, but also 75% or more, 50% or more or 20% or more relative to the case of not introducing an RNAi molecule or the case of having introduced an unrelated control RNAi molecule when evaluating the expression of the target gene by using the mRNA expression level or protein expression level of that gene as an indicator. mRNA expression level can be measured by, for example, northern hybridization or real-time PCR, while protein expression level can be suitably measured by a person with ordinary skill in the art by, for example, western blotting, ELISA or measurement of protein activity. A specific method for measuring gene expression levels is described in Green, M. R. and Sambrook, J. (2012), Molecular Cloning: A Laboratory Manual, Fourth Ed., Cold Spring Harbor Laboratory Press, Cold Spring Harbor, New York.

In the present description, "complementary" refers to a relationship that allows base pairing to occur between two bases (such as that of the Watson-Crick type), and for example, this refers to the relationship between adenine and thymine or uracil and the relationship between cytosine and guanine. In the present description, although being complementary preferably refers to being completely complementary, being completely complementary is not required, but rather an siRNA molecule may contain one or more (such as 1 to 5 or 1 to 3) mismatches provided it retains the ability to suppress expression of a target gene. A mismatch refers to a relationship other than that of adenine and thymine or uracil or that between cytosine and guanine.

An RNAi molecule such as siRNA is generally known to exhibit a high level of RNAi activity in the case of having a single-stranded portion (overhang) of several (such as 2 to 5) nucleotides on the end thereof. Consequently, the siRNA molecule used in the present invention preferably has an overhang of several deoxyribonucleotides or ribonucleotides on the end thereof. For example, the siRNA molecule used in the present invention can have a 3'-overhang consisting of two nucleotides. More specifically, the siRNA molecule used in the present invention may have a 3'-overhang consisting of two ribonucleotides (such as AU (adenine-uracil diribonucleotide) or AG (adenine-guanine diribonucleotide)).

Although the sense strand and antisense strand composing the siRNA molecule used in the present invention may respectively have a base length of, for example, 20 bases to 50 bases, 20 bases to 40 bases or 20 bases to 30 bases, there are no particular limitations thereon and may have mutually the same lengths or different lengths. The siRNA molecule used in the present invention is preferably such that the sense strand and antisense strand respectively have base lengths of 25 bases to 29 bases, and for example, 27 bases.

More specifically, the antisense strand of the siRNA molecule used in the present invention is composed of the base sequence represented by SEQ ID NO: 3, and this is a sequence obtained by adding ribonucleotides AU ((adenine-uracil diribonucleotide) to the 3'-end of the base sequence represented by SEQ ID NO: 1. The sense strand of the siRNA molecule used in the present invention is composed of the base sequence represented by SEQ ID NO: 4, and this is a sequence obtained by adding ribonucleotides AG (adenine-guanine diribonucleotide) to the 3'-end of the base sequence represented by SEQ ID NO: 2.

In addition to the case of the nucleotides of the siRNA molecule used in the present invention all being diribonucleotides, there are cases in which several of the nucleotides (such as 1 to 5 nucleotides, 1 to 3 nucleotides or 1 to 2 nucleotides) are deoxyribonucleotides. In addition to the nucleotides of the siRNA molecule used in the present invention and naturally-occurring nucleotides, the nucleotides may also be modified nucleotides having a group such as a halogen (fluorine, chlorine, bromine or iodine), methyl, carboxymethyl or thio group in order to improve stability of the siRNA molecule.

The sense strand and antisense strand that compose the siRNA molecule used in the present invention can be suitably produced using a commercially available nucleic acid synthesizer. The produced sense strand and antisense strand may be preferably mixed at an equimolar ratio and mutually hybridized to produce the siRNA molecule used in the present invention. In addition, the siRNA molecule can also be produced by using the commissioned production service of a manufacturer (such as BioSpring, Takara Bio or Sigma-Aldrich).

The siRNA that suppresses expression of CHST15 gene contained in the pharmaceutical composition for the treatment and/or prevention of a chronic disease of the present invention contains a structure formed by the hybridization of an antisense RNA having the nucleotide sequence represented by SEQ ID NO: 1 with a sense RNA having the nucleotide sequence represented by SEQ ID NO: 2, or is composed of that structure. The nucleotide sequence represented by SEQ ID NO: 1 is complementary to the nucleotide sequence represented by SEQ ID NO: 2. The siRNA named STNM01 in the examples of the description of the present application is composed of a structure formed by the hybridization of an antisense RNA strand having the nucleotide sequence represented by SEQ ID NO: 3 with a sense RNA strand having the nucleotide sequence represented by SEQ ID NO: 4. The nucleotide sequence represented by SEQ ID NO: 3 is complementary to the nucleotide sequence represented by SEQ ID NO: 4. RNA having the nucleotide sequence represented by SEQ ID NO: 3 has the diribonucleotide AU bound to the 3'-end of a ribonucleotide having the nucleotide sequence represented by SEQ ID NO: 1. RNA having the nucleotide sequence represented by SEQ ID NO: 4 has the diribonucleotide AG bound to the 3'-end of a ribonucleotide having the nucleotide sequence represented by SEQ ID NO: 2. The nucleotide sequence represented by SEQ ID NO: 2 is a partial sequence of the cDNA sense strand deoxyribonucleotide sequence of human CHST15 represented by SEQ ID NO: 5. SEQ ID NO: 5 can be acquired as GenBank Accession No. NM_015892 (Version: NM_015892.4).

The pharmaceutical composition for the treatment and/or prevention of a chronic disease of the present invention may contain any formulation auxiliary agent normally used in the field of pharmaceuticals. Various drug carriers or additives may be used as a formulation auxiliary agent, examples of which include pharmaceutically acceptable carriers (either solid or liquid carriers), vehicles, stabilizers, emulsifiers, surfactants, binders, disintegration agents, lubricants, smell correctives, solubilizing agents, suspensions, coating agents, coloring agents, flavor correctives, preservatives and buffers. More specifically, examples of formulation auxiliary agents include water, physiological saline, other aqueous solvents, pharmaceutically acceptable organic solvents, mannitol, microcrystalline cellulose, starch, glucose, calcium, polyvinyl alcohol, collagen, polyvinylpyrrolidone, carboxyvinyl polymer, sodium alginate, water-soluble dextran, water-soluble dextrin, sodium carboxymethyl starch, gum arabic, pectin, xanthan gum, casein, gelatin, agar, propylene glycol, glycerin, polyethylene glycol, Vaseline, paraffin, stearyl alcohol, stearic acid, sorbitol and lactose. The formulation auxiliary agent may be suitably selected or combined corresponding to the dosage form of the preparation.

Although the pharmaceutical composition for the treatment and/or prevention of a chronic disease of the present invention may be administered orally or parentally (such as by transrectal administration, transmucosal administration, intravenous administration, intraarterial administration or percutaneous administration), it may be particularly administered by oral administration or transrectal administration.

Examples of dosage forms suitable for oral administration include solid preparations (such as tablets, pills, sublingual preparations, capsules, lozenges or drops), granules, powders and liquids. Solid preparations may be dosage forms provided with a coating known in the art, examples of which include sugar-coated tablets, gelatin-coated tablets, enteric-coated tables, film-coated tablets, double-layered tablets and multilayered tablets. These coatings may be provided for the purpose of causing the release of an active ingredient at a target location in the body or enhance absorption of an active ingredient.

A dosage form suitable for each administration method can be suitably used in the case of parenteral administration, and examples of dosage forms suitable for parenteral administration include suppositories, injections, infusions, coating agents, eye drops, nasal drops, inhalants, suspensions, emulsions, creams, pastes, gels, ointments and plasters.

The pharmaceutical composition for the treatment and/or prevention of a chronic disease of the present invention can be administered to a body in a pharmaceutically effective amount for treating or preventing a target disease. In the present description, a "pharmaceutically effective amount" refers to the dose required for the siRNA contained in the pharmaceutical composition of the present invention to treat or prevent a target disease without having hardly any or no adverse side effects on the body receiving administration. The specific dose is determined at, for example, the discretion of a physician corresponding to the individual subject based on such factors as the progression or severity of the disease, general health, age, gender, body weight or tolerance to the treatment. For example, in the case of orally administering the pharmaceutical composition of the present invention, the pharmaceutical composition may be administered based on the weight of the siRNA molecule that suppresses expression of CHST15 gene, and is normally administered in an amount at which the weight of the siRNA molecule is 0.001 to 1000 mg/kg of body weight per a day, and for example, 0.01 to 100 mg/kg of body weight per a day or 0.1 to 10 mg/kg of body weight per a day. Although the pharmaceutical composition of the present invention can be administered in a single administration based on a treatment plan determined by a physician, it can also be administered to a subject by dividing among several or several tens of administrations at a fixed time interval such as an interval of 1 day, 2 days, 3 days, 4 days, 5 days, 6 days, 1 week, 2 weeks, 3 weeks, 1 month, 2 months, 6 months or 1 year.

In the present invention, "treatment" refers to the healing, alleviation or improvement of a disease or symptoms, while "prevention" refers to the inhibition, suppression or delay of a disease or symptoms.

Since the mechanism of action of the pharmaceutical composition for the treatment and/or prevention of a chronic disease of the present invention is inhibition of rolling, which is the first stage of hematogenous tissue invasion by leukocytes, the combined use of the pharmaceutical composition for the treatment and/or prevention of a chronic disease of the present invention with a pharmaceutical effective against chronic disease by a mechanism of action that inhibits stages downstream from the first stage or a mechanism of action independent from hematogenous tissue invasion by leukocytes allows the obtaining of higher efficacy.

A biological preparation that inhibits hematogenous tissue invasion by leukocytes and can be used in combination with the pharmaceutical composition for the treatment and/or prevention of a chronic disease of the present invention may be any biological preparation on the condition that it has for the mechanism of action thereof the inhibition of a stage downstream from the first stage of hematogenous tissue invasion by leukocytes. The aforementioned biological preparation may have as its mechanism of action thereof, for example, the inhibition of at least one stage among the second stage of leukocyte hematogenous tissue invasion in the form of chemokine stimulation, the third stage of strong adhesion by integrin and/or the fourth stage of extravascular migration. Examples of biological preparations that stimulate chemokines in the second stage of leukocyte hematogenous tissue invasion include, but are not limited to, CCR9. Hematogenous tissue invasion by leukocytes is reduced or suppressed by inhibiting the function of chemokine receptors. Examples of biological preparations that inhibit strong adhesion by integrin in the third stage of leukocyte hematogenous tissue invasion include, but are not limited to, the β7 subunit of α4β7 and αEβ7, α4β7 integrin (LPAM-1) and/or the integrin α4 subunit, and hematogenous tissue invasion by leukocytes is reduced or suppressed by inhibiting the function of integrin on the surface of lymphocytes in the circulating blood. Examples of biological preparations that inhibit extravascular migration of the fourth stage of leukocyte hematogenous tissue invasion include, but are not limited to, MAdCAM. Hematogenous tissue invasion by leukocytes is reduced or suppressed by inhibiting the function of adhesion molecules on the surface of vascular endothelial cells.

A biological preparation that inhibits inflammatory cytokines and can be used in combination with the pharmaceutical composition for the treatment and/or prevention of a chronic disease of the present invention may inhibit the function of at least one inflammatory cytokine involved in a chronic disease. Examples of the aforementioned inflammatory cytokines include, but are not limited to, TNF-α, IL-1β, Il-17, IL-18, IL-23 and GM-CSF. The aforementioned inflammatory cytokine may be at least one of TNF-α, IL-17 and IL-23. The aforementioned biological preparation that inhibits inflammatory cytokines may be an antibody that inhibits the aforementioned inflammatory cytokines, an antibody fragment, or a specific binding partner for the aforementioned inflammatory cytokines such as a single-domain antibody.

Examples of anti-inflammatory agents, immunomodulators or immunosuppressants used in combination with the pharmaceutical composition for the treatment and/or prevention of a chronic disease of the present invention include, but are not limited to, 5-aminosalicyclic acid preparations in the manner of Pentasa, Salazopyrin, Asacol and Lialda, steroid preparations in the manner of Rinderon and Predonema, thiopurine preparations in the manner of azathioprine and 6-MP, and immunosuppressants in the manner of tacrolimus and cyclosporine.

It is disclosed in WO 2017/078054 by the inventor of the present application that, when a complex containing N-acetylated chitosan and siRNA of the active ingredient of the pharmaceutical composition for the treatment and/or prevention of a chronic disease of the present invention is administered orally, the complex is efficiently delivered to the digestive tract and suppresses the expression of CHST15 gene, and demonstrates therapeutic efficacy against inflammation of the digestive tract, and particularly chronic inflammation. The method for preparing the aforementioned complex is also disclosed in WO 2017/078054.

More concisely, chitosan is a high molecular weight polysaccharide having a structure consisting of a mixture of glucosamine and a small amount of N-acetylglucosamine. Chitosan can be obtained by deacetylating chitin, which can be obtained from crustaceans such as crab or shrimp, by heating with a concentrated alkaline solution. Chitosan is commercially available from such manufacturers as Carbosynth or Funakoshi in various degrees of acetylation and molecular weights. The degree of acetylation of chitosan in the present description can be normally 0% to 30%, and for example, 20% or less 10% or less or 5% or less. In the present description, there are no particular limitations on the molecular weight of chitosan, and may be low molecular weight chitosan (such as that having a molecular weight of 2000 Da to 100 kDa), high molecular weight chitosan (such as that having a molecular weight of 100 kDa to 10,000 kDa) or chitosan consisting of a mixture of various molecular weights.

N-acetylated chitosan is a high molecular weight polysaccharide obtained by acetylating all or a portion of the amino groups of the aforementioned chitosan. In the present description, the degree of acetylation of N-acetylated chitosan is normally 70% to 100%, and for example, 80% or more, 90% or more, 95% or more, 98% or more or 99% or more. The degree of acetylation of chitosan and N-acetylated chitosan can be determined by such methods as colloid titration, infrared absorption spectroscopy, nuclear magnetic resonance (NMR) or elemental analysis.

Although there are no particular limitations on the bonding form between the siRNA and N-acetylated chitosan in a complex containing N-acetylated chitosan and siRNA of the active ingredient of the pharmaceutical composition for the treatment and/or prevention of a chronic disease of the present invention, since RNAi molecules are anionic polymers and N-acetylated chitosan is a cationic polymer, the two components are presumed to form a complex through electrostatic interaction. In the aforementioned complex, the ratio (molar ratio) of RNAi molecules to glucosamine units composing N-acetylated chitosan is 1:200 to 1:5, 1:100 to 1:5 or 1:50 to 1:10.

The aforementioned complex is able to deliver the RNAi molecule to cells by a non-invasive administration method such as oral administration without requiring a special drug delivery system.

In the present invention, "administering in combination" refers to the simultaneous administration of a biological preparation that inhibits hematogenous tissue invasion by leukocytes and/or a biological preparation that inhibits inflammatory cytokines, at least one member selected from the group consisting of anti-inflammatory agents, immunomodulators and immunosuppressants in the form of 5-aminosalicylic acid, steroid preparations, thiopurine preparations and immunosuppressants including tacrolimus and cyclosporine depending on the case, and the pharmaceutical composition of the present invention either continuously or after allowing a certain period of time after having administered one of the above. In the case of administering a biological preparation that inhibits hematogenous tissue invasion by leukocytes and/or a biological preparation that inhibits inflammatory cytokines, at least one member selected from the group consisting of anti-inflammatory agents, immunomodulators and immunosuppressants in the form of 5-aminosalicylic acid, steroid preparations, thiopurine preparations and immunosuppressants including tacrolimus and cyclosporine depending on the case, and the pharmaceutical composition of the present invention, overlapping of the administration period of the pharmaceutical composition of the present invention and the administration period of either of the aforementioned biological preparations, or administration of the pharmaceutical composition of the present invention within a period equal to at least 20% of the administration period of the biological preparation following completion of the administration period of the biological preparation, is included in "administration in combination". Although the dose of the pharmaceutical composition of the present invention can be suitably adjusted according to such factors as body weight, age and symptoms of the subject to receive administration, in the case, for example, the biological preparation is an antibody, the dose is, for example, 0.1 mg/kg/week to 100 mg/kg/week or a dose that yields a blood concentration equivalent thereto, preferably 1 mg/kg/week to 50 mg/kg/week or a dose that yields a blood concentration equivalent thereto, and more preferably 5 mg/kg/week to 10 mg/kg/week or a dose that yields a blood concentration equivalent thereto. In addition, the dose of, for example, the aforementioned anti-inflammatory agent, immunomodulator or immunosuppressant is, for example, 10 mg/m$^2$/week to 10000 mg/m$^2$/week or a dose that yields a blood concentration equivalent thereto, preferably 100 mg/m$^2$/week to 5000 mg/m$^2$/week or a dose that yields a blood concentration equivalent thereto, and more preferably 500 mg/m$^2$/week to 1500 mg/m$^2$/week or a dose that yields a blood concentration equivalent thereto.

An administration method, administration interval and dose that yield a therapeutic effect similar to the effect of the present invention can be suitably selected for the aforementioned administration method, administration interval and dose. For example, an administration method, administration interval and dose that yield an effect similar to that of the aforementioned preferable examples can be selected by measuring the blood concentrations of a biological preparation that inhibits hematogenous tissue invasion by leukocytes and/or a biological preparation that inhibits inflammatory cytokines, at least one member selected from the group consisting of anti-inflammatory agents, immunomodulators and immunosuppressants in the form of 5-aminosalicylic acid, steroid preparations, thiopurine preparations and immunosuppressants including tacrolimus and cyclosporine depending on the case, and the pharmaceutical composition of the present invention, and an administration method, administration interval and dose that achieve a blood concentration equivalent to that of the aforementioned examples are included in the present invention.

In the present description, examples of diseases used for treatment and/or prevention by the pharmaceutical composition of the present invention include, but are not limited to, Guillain-Barrê syndrome, myasthenia gravis, chronic gastritis, chronic atrophic gastritis, autoimmune hepatitis, primary biliary cholangitis, inflammatory bowel disease, Crohn's disease, ulcerative colitis, autoimmune pancreatitis, Takayasu's arteritis, Goodpasture's syndrome, rapidly progressive glomerulonephritis, Grave's disease, Hashimoto's thyroiditis, primary hypothyroidism, idiopathic Addison's disease, type 1 diabetes, chronic discoid lupus erythematosus, localized scleroderma, pemphigus, pustular psoriasis, psoriasis vulgaris, acquired epidermolysis bullosa, autoimmune optic neuropathy, chronic rheumatoid arthritis, systemic lupus erythematosus, scleroderma, polymyositis, dermatomyositis, vasculitis syndrome, mixed connective tissue disease, bronchial asthma, chronic thyroiditis and atopic dermatitis.

A detailed explanation of the present invention and its examples are also explained by the following references included in the submitted documents of the present application and documents cited therein.

In particular, references consisting of Suzawa, K., et al., Am. J. Gastroenterol. 2007; 102: 1499-1509, Yeh, J. C., et al., Cell, 2001; 105: 957-969, Kobayashi, M., et al., Biol. Pharm. Bull. 2009; 32: 774-779, and A. van Zante and S. D. Rosen, Biochemical Society Transactions 2003; 31: 313-317 are incorporated in their entirety in the present description by reference.

The subsequently explained examples of the present invention are provided for the purpose of exemplification only and are not intended to limit the technical scope of the present invention. The technical scope of the present invention is only limited by the description of the claims. The present invention can be modified, such as by adding, deleting or interchanging constituent elements of the present invention, under the condition that such modifications do not deviate from the gist of the present invention.

The following provides an explanation of the results of a phase IIa clinical trial described in Example 1 consisting of single-dose administration of the pharmaceutical composition of the present invention by submucosal injection into ulcerative colitis patients currently not taking biological preparations, and the results of an investigator initiated trial described in Example 2 consisting of multiple-dose administration of the pharmaceutical composition of the present invention by submucosal injection into ulcerative colitis patients currently taking biological preparations.

Example 1

The following provides an explanation of a clinical trial of the pharmaceutical composition of the present invention based on Sections 8 and 9 of the phase IIa clinical trial protocol of STNM01. Furthermore, in the following explanation, although terms such as "will be" representing the future tense are used in the description of the trial protocol, the clinical trial was actually completed by the filing date of the present application.

Clinical Trial Protocol Section 8—Trial Design and Scheduled Sample Size 8.1 Trial Design This clinical trial is a randomized double-blind, placebo-controlled parallel-group trial of STNM01 by single-dose submucosal injection.

Freeze-dried STNM01 will be diluted using physiological saline. The trial drug will be administered submucosally into the rectosigmoid colon using an endoscope. The patients will be randomized so as to receive STNM01 (a concentrations of 25 nM and 250 nM) or a placebo. The subjects will receive a single dose of the trial drug on day 1. The subjects will be discharged on day 2 after having been confirmed to be free of any safety concerns. The subjects will return to the trial facility for testing to observe progress 14 days and 28 days after administration. Table 1 shows the doses (concentrations), dosing schedule and numbers of subjects.

TABLE 1

| Group | 1 | 2 | 3 |
|---|---|---|---|
| Trial drug | STNM01 | STNM01 | placebo |
| Concentration (nM) | 25 | 250 | ... |
| No. of subjects | 8 | 8 | 8 |
| No. of administrations | Single-dose administration | | |
| Dosing schedule | The trial drug will be injected submucosally into the rectosigmoid colon containing all possible constricted lesions using an endoscope and endoscopic puncture needle (22G). | | |
| Dose | Maximum of 2 mL per site by single injection; total of a maximum of 16 mL per lesion (as explained in Scheme 10.1 of Section 10.5.2, a total of 8 sites from lesions decreasing from 35 cm to 5 cm: SIC002 Injection Model) | | |

<Rationale>

Local administration of STNM01 (including 25 nM and 250 nM) in a completely randomized, double-blind placebo-controlled phase I clinical trial generally indicated favorable tolerance. For this reason, there are no concerns over safety whatsoever that would impair implementation of parallel-group phase IIa clinical trial proposed at this time. Since the primary purpose of the phase I clinical trial was to evaluate safety, the mucosa healing effect observed in the phase I clinical trial was unexpected. Thus, the purpose of the scheduled phase IIa clinical trial is to confirm the effects observed in the phase I clinical trial, and obtain more information relating to efficacy parameters and the dose to be used in a subsequent larger controlled trial scheduled to be implemented. Although the design is a parallel-group comparative design, patient safety will be closely monitored and evaluated as a second evaluation parameter.

8.2 Discontinuation and Interruption of Clinical Trial

In the case serious or grave adverse side effects thought to have been caused by a factor other than the trial drug, such as the trial procedure, have occurred in one or more subjects in the current step, or in the case moderate adverse side effects requiring medical intervention thought to have been caused by a factor other than the trial drug have occurred in more than half of the subjects in the current step, the sponsor will temporarily discontinue the trial and examine continuation of the trial in consideration of the opinion of the trial director.

8.3 Scheduled Sample Size

In the case of a sample size of 8 per group (assuming a withdrawal rate of 15%), a $\chi^2$ test of two groups having a two-sided significance level of 0.050 will have statistical power of 80% in order to detect the difference between the effective procedure and a placebo (89% vs. 11%). For this reason, 8 subjects per group (8 subjects for STNM01 at 25 nM, 8 subjects for STNM01 at 250 nM, and 8 subjects for the placebo), or in other words, a total of 24 subjects, will be included.

8.4 Scheduled Trial Period

May 2013 to May 2016

Discussion of Trial Design and Selection of Control Group

This is a phase IIa clinical trial for investigating the safety and efficacy of a single dose of STNM01. The trial design is thought to be appropriate for a trial of this type.

9. Selection and Discontinuation/Withdrawal of Subjects

Participation in the trial will be based on being qualified in accordance with the selection criteria and exclusion criteria, whether or not patients are patients of the participating facility will be verified with the participating facility and presented to the trial director, and participation will be recommended to all patients.

9.1 Indications

Patients with ulcerative colitis having endoscopically active lesions (group).

9.2 Selection Criteria and Exclusion Criteria 9.2.1 Selection Criteria

Subject eligibility will be determined in accordance with the criteria indicated below.

1) Men/women
2) Subjects are ulcerative colitis patients having active lesions (group).
3) Subjects are treated with a customary drug (group) commonly used to treat ulcerative colitis at least two months prior to a screening test [such as a 5-aminosalicylic acid agent, steroid, immunomodulator or biological agent (for example, anti-TNF antibody or Vedolizumab requires a washout period of 4 weeks)]. According to the opinion of the attending physician, an insufficient response or tolerance occurred with respect to one of the current customary treatment choices. An insufficient response or tolerance exhibited by a subject to the current treatment is confirmed by the supervising study director of this trial based on screening tests that include an endoscopic examination, medical examination and clinical testing. Although an "insufficient response or tolerance" experienced by a subject can be evaluated by the attending physician and supervising trial director, insufficient therapeutic efficacy attributable to the use of one prescribed pharmacotherapy and the current pharmacotherapy (group) is to be recorded in the subject's chart.
4) Even if a subject does not present with hardly any difficulty in inserting the endoscope, such as the subject exhibiting hardly any constriction or even if constriction is present, the diameter of the constricted lesion is 14 mm or less.
5) The Mayo endoscopic score during screening must be 1 or must exceed 1.
6) The age of the subjects is 18 to 65 years old at the time of informed consent.
7) Subjects are to sign and date a written informed consent in order to participate in the trial.

<Rationale>

2) The endoscopic severity of the ulcerative colitis is to be from moderate to severe. This is because the trial requires treatment of in-patients and patients to be examined as out-patients using the trial drug.

3) This is for investigating the efficacy and safety of the trial drug in the case of customary treatment and concomitant administration.

4,5) This is for implementing the trial while strictly observing the protocol.

6) This is for strictly observing GCP.

9.2.2 Exclusion Criteria

Any subject satisfying any of the following criteria will be ineligible to participate in the trial.

1) The subject has a serious heart disease, hematological disease or lung disease or has a history of such, and the trial supervisor indicates the opinion that participation in the trial by that subject is inappropriate.
2) The subject has a history of colectomy for treatment of ulcerative colitis.
3) The subject has complications of ulcerative colitis such as severe bleeding or intestinal adhesions with other organs, and the trial supervisor indicates the opinion that participation in the study is inappropriate.
4) The subject has anal stenosis that affects defecation frequency or has a perianal abscess accompanied by fever. However, the subject is eligible to participate in the trial in the case intestinal movement is improved according to the Seton method.
5) The general condition of the subject has clearly declined.
6) Subjects in which the majority of the colon is affected by disease (pancolitis).
7) Subjects predicted to present with symptoms requiring colectomy during participation in the trial.
8) The subject is currently undergoing total parenteral nutrition.
9) The subject has liver damage or kidney damage, and the trial supervisor indicates the opinion that participation in the trial is inappropriate.
10) The subject has had a malignant tumor within the past five years or as a history of such.
11) The subject has intestinal tuberculosis or has a history of such.
12) The subject has serious complications due to infection that require hospitalization.
13) The subject is to be excluded if currently being treated using a biological preparation (such as anti-TNF-α antibody or vedolizumab.
14) The subject is to be excluded if being treated using concomitant pharmacotherapy by local administration (such as a 5-aminosalicylic acid agent, steroid or immunomodulator).
15) The subject has a history of clinically severe allergy symptoms. "Severe" refers to allergic symptoms causing generalized urticaria, anaphylactic shock or shock requiring hospitalization in the case of having been exposed to a specific antigen or drug.
16) The subject has a history of HBV, HCV and/or HIV infection.
17) The subject has alcohol or drug dependency.
18) Customary treatment of the subject for ulcerative colitis is such that the "quality" of the treatment plan (drug class) has changed or a new treatment has been added: There has been no introduction of thiopurine whatsoever during the past three months and there is no change in administration of 5-ASA or adrenocortical steroids for 14 days prior to administration of the trial drug.
19) The subject is currently participating in a different clinical trial while this trial is in progress or plans on participating in such a trial.
20) The subject has been administered any other trial drug preparation within six months prior to giving informed consent to participate in this trial.
21) The subject has any mental illness or neurological disorder and the trial supervisor indicates the opinion that participation in the trial is inappropriate.
22) The subject is unable to undergo an examination or procedure directed according to the protocol or is restricted from doing so.
23) The subject is judged to be unsuitable for participation in this clinical trial by the trial supervisor for any other reason.
24) The subject does not desire to or is unable to (Pearl index of less than 1) use a reliable and acceptable method of contraception. Each of his or her sexual partners must use at least one of these reliable methods of contraception from six months before until 3 weeks after administration of the trial drug.
25) Women: Pregnant or lactating.
26) Colleagues, students, relatives or spouse of the trial director.

<Rationale>

1) to 20) These are for ensuring the safety of the subjects and eliminating effects on evaluating safety and efficacy of the trial drug.
21) Subjects presenting with these disease states are excluded. This is because a report is required of subjective symptoms of subjects that can be impaired by mental illness or neurological disorder.
22) This is for implementing the clinical trial while strictly observing the protocol.
23) This is to exclude individuals for whom it has been judged to be medically or ethically inappropriate to participate in the clinical trial for reasons other than those described in 1) to 21).

9.3 Prior and Concomitant Pharmacotherapy and Therapy Methods

1) Only systemic concomitant pharmacotherapy is permitted. The use of locally administered background therapy is prohibited [such as a 5-ASA, steroids, immunomodulators or biological agents (for example, anti-TNF antibody or Vedolizumab requires a washout period of 4 weeks)].
2) All pharmacotherapy used during the time from two months before administration of the trial drug to the time of completion of the clinical trial are to be recorded in the case report (including the name of the drug, purpose, daily dose, administration schedule, administration route and initiation and termination dates).
3) Pharmacotherapy for treating ulcerative colitis used prior to the period described in 1) above will be recorded in the same manner if possible.
4) All treatments other than pharmacotherapy will be recorded in the case report if possible (including treatment method, purpose and initiation and termination dates).
5) All pharmacotherapy and treatments for treating harmful events that are used prior to completion of the final observation or examination of this clinical trial are to be recorded in the case report. The use of pharmacotherapy and treatments for emergencies will be treated as a deviation from the protocol.

<Rationale>

The concomitant use of preliminary pharmacotherapy and treatments in this clinical trial using STNM01 is justifiable. This is because only an extremely small number of toxic findings have been observed and the trial drug was rapidly eliminated from the blood following administration in a non-clinical trial of STNM01, and therefore, we presume that the occurrence of unknown harmful drug reactions or increases in the severity of harmful drug reactions of prior pharmacotherapy will not occur.

9.4 Restrictions During Clinical Trial

Subjects must be advised to follow the instructions indicated below. Subjects will remain under the medical supervision of the trial supervisor while hospitalized.

9.4.1 Food, Beverages, Smoking and Exercise

Subjects will fast starting after the evening meal on day 0 until 4 hours after administration of the trial drug on day 1. Subjects will also fast starting after the evening meal on the day before testing for observing progress to the day of their completion.

Foods and beverages containing alcohol or caffeine will be prohibited during hospitalization. Following discharge, excessive consumption of water will be prohibited until completion of the final examination or observation. Alcoholic beverages will not be permitted starting on the day before examinations for monitoring progress until the day of their completion.

Food and beverages other than those served at the trial facility will not be allowed during hospitalization. Subjects must be instructed to refrain from excess consumption of food and water starting after their discharge to completion of the final examination or observation.

Smoking will be prohibited during hospitalization. Smoking will not be permitted from going to bed on the day before monitoring of progress until the day of its completion.

Physical exercise will be prohibited during the time the subject is in the trial facility and from the day before examinations for monitoring progress until the day of their completion.

9.4.2 Contact with Subjects after Discharge

The management organization of the facility will contact subjects in a timely manner prior to scheduled visits to the facility with respect to the trial procedure that requires monitoring of progress (such as restrictions relating to excessive consumption of food and water after being discharged).

Criteria for Subject Discontinuation or Withdrawal

In the case of any of the circumstances indicated below, the trial supervisor must immediately discontinue administration of the trial drug to subjects, provide appropriate treatment to the subjects, and implement as many of the examinations and observations scheduled at the time of discharge as possible. Subjects that have withdrawn from the trial at an intermediate time period may be replaced. The trial supervisor will record the date and reason for discontinuation, treatment administered after discontinuation and subsequent clinical progress in the case report (and this must be submitted to the sponsor without delay). In the case scheduled examinations and observations were unable to be performed at the time of discontinuation, that reason must be recorded in the case report.

1) A subject has retracted consent.
2) A subject has not satisfied the participation criteria of the protocol.
3) The trial director has judged a subject will suffer a loss if he or she continues to participate in the clinical trial (such as the occurrence of a harmful event or exacerbation of the primary disease requiring termination of the clinical trial).
4) When there has been a significant deviation from the protocol.
5) The sponsor has terminated the trial at an intermediate point.
6) The trial director has found it to be necessary to exclude a subject from the trial for a reason other than that previously indicated.

<Rationale>

1) This is the one requirement for obtaining informed consent.
2) Subjects for whom suitable evaluations cannot be obtained are to be excluded from the trial.
3) This is for considering safety and ethics.
4) Significant deviations from the protocol are in violation of good clinical practice.
5) This will be applied in the case the sponsor has determined that all research it to be terminated or discontinued.
6) This is for excluding subjects from the trial in the case the trial director has judged it to be necessary for reasons other than those described above.

1. Evaluation of Endoscopic and Histopathological Therapeutic Effects

Subjects screened based on sections 8 and 9 of the phase IIa clinical trial protocol were given a single administration of STNM0 at 250 nM or 25 nM or a placebo by intestinal submucosal injection with an endoscopic puncture needle as shown in Table 1. Lesions were examined endoscopically at the time of administration and in weeks 2 and 4. The results of endoscopic examinations were evaluated according to the Mayo endoscopic sub-score (Colombel, J. F., et al., Gastroenterology 2011; 141: 1194-1201). The number of subjects in each dose group was 8 for each group as shown in Table 1. In addition, biopsy tissue samples at the lesion site were harvested from the subjects immediately before administration and in week 4 of administration, hematoxylin-eosin-stained tissue specimens were prepared and histopathological examinations were performed. These results are shown in the endoscopic photographs and photomicrographs of the tissue specimens shown in FIG. 2. Moreover, changes in the Mayo endoscopic sub-scores of the subjects in each group are represented with the graph shown on the right side of FIG. 2.

Figure 2:
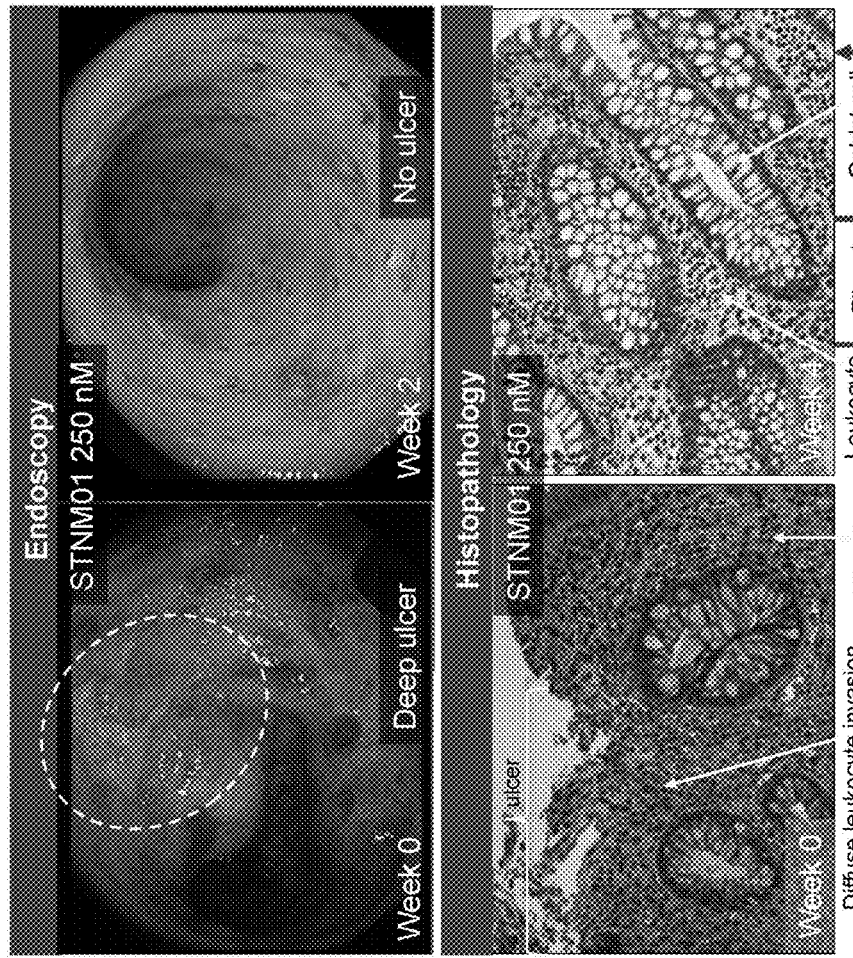
FIG. 2 depicts data indicating the results for the primary evaluation parameter (mucosal healing) obtained in a phase IIa clinical trial of the pharmaceutical composition of the present invention against ulcerative colitis.

The subject shown in the endoscopic photographs at the top of FIG. 2 and photomicrographs shown at the bottom of FIG. 2 was endoscopically observed to have an antibody preparation-resistant, deep ulcer at the time of administration even when the biological preparation is administered, and diffuse leukocyte invasion and fibrosis were observed even in histopathological examinations. However, the ulcer had disappeared in endoscopic observations performed in week 2, and signs of inflammation had disappeared in histopathological examinations performed in week 4. As indicated by the graph on the right side of FIG. 2, the 250 nM STNM01 dose group exhibited a significantly decreased Mayo endoscopic sub-score in comparison with the 25 nM STNM01 dose group or placebo dose group. Based on the results of FIG. 2, administration of STNM01 at 250 nM was verified to demonstrate a high level of therapeutic efficacy.

2. Evaluation of Effect on Sulfation of L-Selectin Ligand

Immunohistostaining with MECA-79 antibody that specifically detects sulfated L-selectin ligand was performed in the manner indicated below (Yeh, J.-C., et al., Cell, 2001, 105; 957-969). The number of subjects in each dose group was 8 for all groups as shown in Table 1. Intestinal biopsy tissue samples recovered from all subjects were embedded in paraffin, thinly sectioned and removed of paraffin followed by immersing for 5 minutes in 0.03% $H_2O_2$ to inhibit endogenous peroxide activity. Subsequently, the samples were incubated for 10 minutes in a blocking agent for use in immunological testing in the form of Block Ace (DS Pharma Biomedical Co., Ltd.). The sections were subsequently incubated at 4° C. with a 200-fold dilution of MECA-79 antibody (R&D Systems, USA). After incubating with secondary antibody (HIRP-labeled anti-goat IgG), an enzymatic color reaction was performed using a solution of 3,3'-diaminobenzidine and $H_2O_2$. Quantitative analysis was carried out by photographing bright field images of the MECA-79 stained sections with a digital camera at a magnification factor of 200×. The area of the positive portions of four fields per section was measured using Image J Software (NIH, USA). The means and standard errors of the percentages of the area of the positive portions of intestinal biopsy tissue specimens of each dose group are shown in the graph on the right side of FIG. 3.

Figure 3:
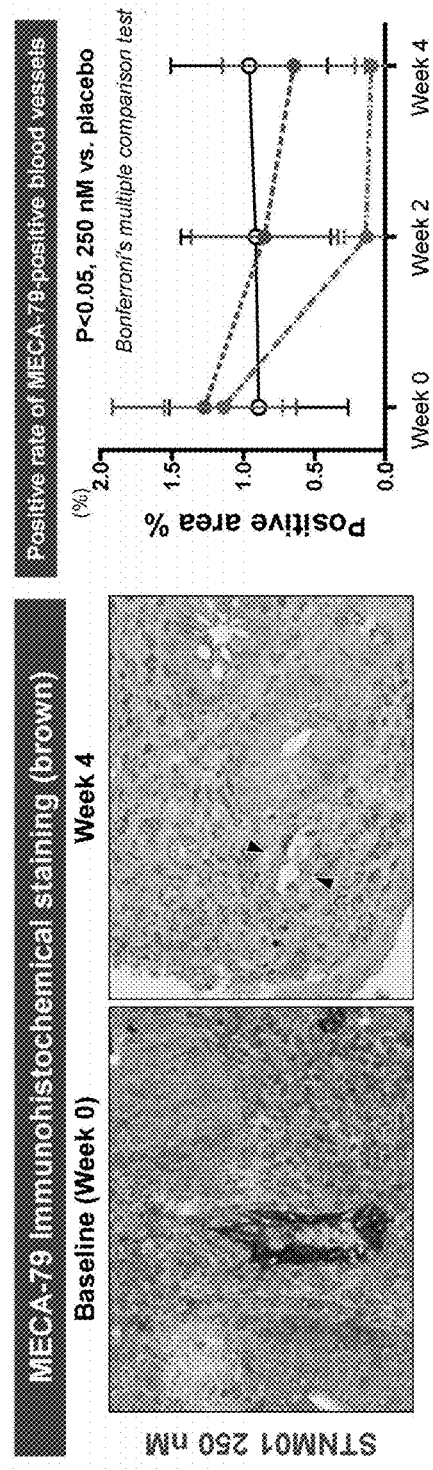
FIG. 3 depicts data indicating a decrease in sulfation of L-selectin ligand obtained in a phase IIa clinical trial of the pharmaceutical composition of the present invention against ulcerative colitis.

MECA-79-positive blood vessels were detected in the subject indicated in the photomicrographs following immunohistochemical staining with MECA-79 antibody shown on the left side of FIG. 3 during administration of STNM01 (week 0) despite having been administered a biological preparation. However, MECA-79-positive blood vessels were not detected in week 4 after administration of STNM01. As shown in the graph on the right side of FIG. 3, the 250 nM STNM01 dose group demonstrated a significant decrease in the percentage of the area of the positive portion in comparison with the placebo group. Based on the results of FIG. 3, administration of STNM01 at 250 nM was verified to decrease sulfation of L-selectin ligand.

3. Evaluation of Effect on Lymphocyte Hematogenous Invasion

In order to evaluate the effect on lymphocyte hematogenous invasion, intestinal biopsy tissue samples collected from all 8 subjects of each dose group were embedded in paraffin, sliced into thin sections and paraffin was removed from the resulting sections followed by staining with hematoxylin-eosin stain. Bright field images of the sections were photographed with a digital camera at a magnification factor of 200× in the same manner as the bright field images of the M ECA-79 stained sections described in the previous section. The area of the positive portions of four fields per section was measured using Image J Software (NIH, USA). The means and standard errors of the number of basement membrane lymphocytes per 100 $sm^2$ are shown in the graph of FIG. 4.

Figure 4:
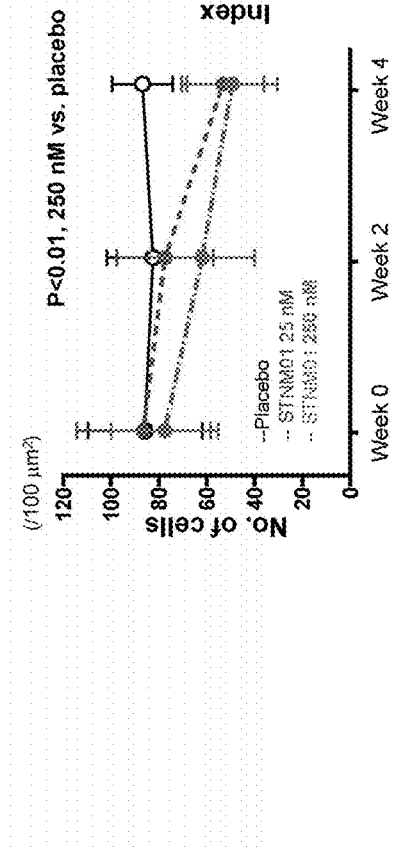
FIG. 4 depicts data indicating a reduction in lymphocyte infiltration obtained in a phase IIa clinical trial of the pharmaceutical composition of the present invention against ulcerative colitis.

As shown in the graph of FIG. 4, the 250 nM STNM01 dose group demonstrated a significant decrease in the number of basement membrane lymphocytes as compared with the placebo dose group. Based on the results of FIG. 4, administration of STNM01 at 250 nM was verified to decrease tissue invasion by lymphocytes.

Figure 5:
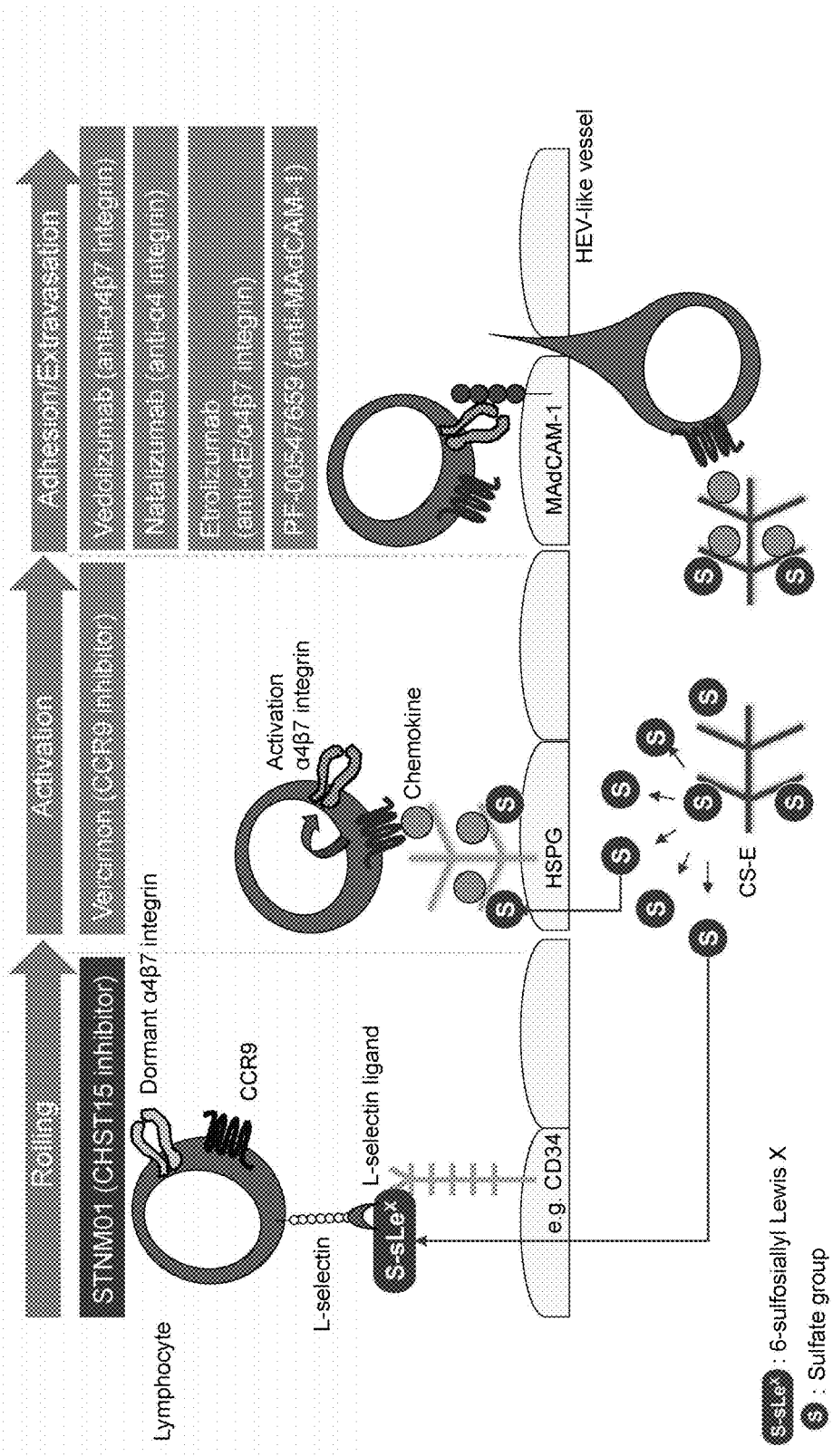
FIG. 5 is a schematic diagram indicating points of action of the pharmaceutical composition of the present invention and existing therapeutic drugs for an inflammatory chronic disease during tissue invasion by leukocytes.
Figure 6:
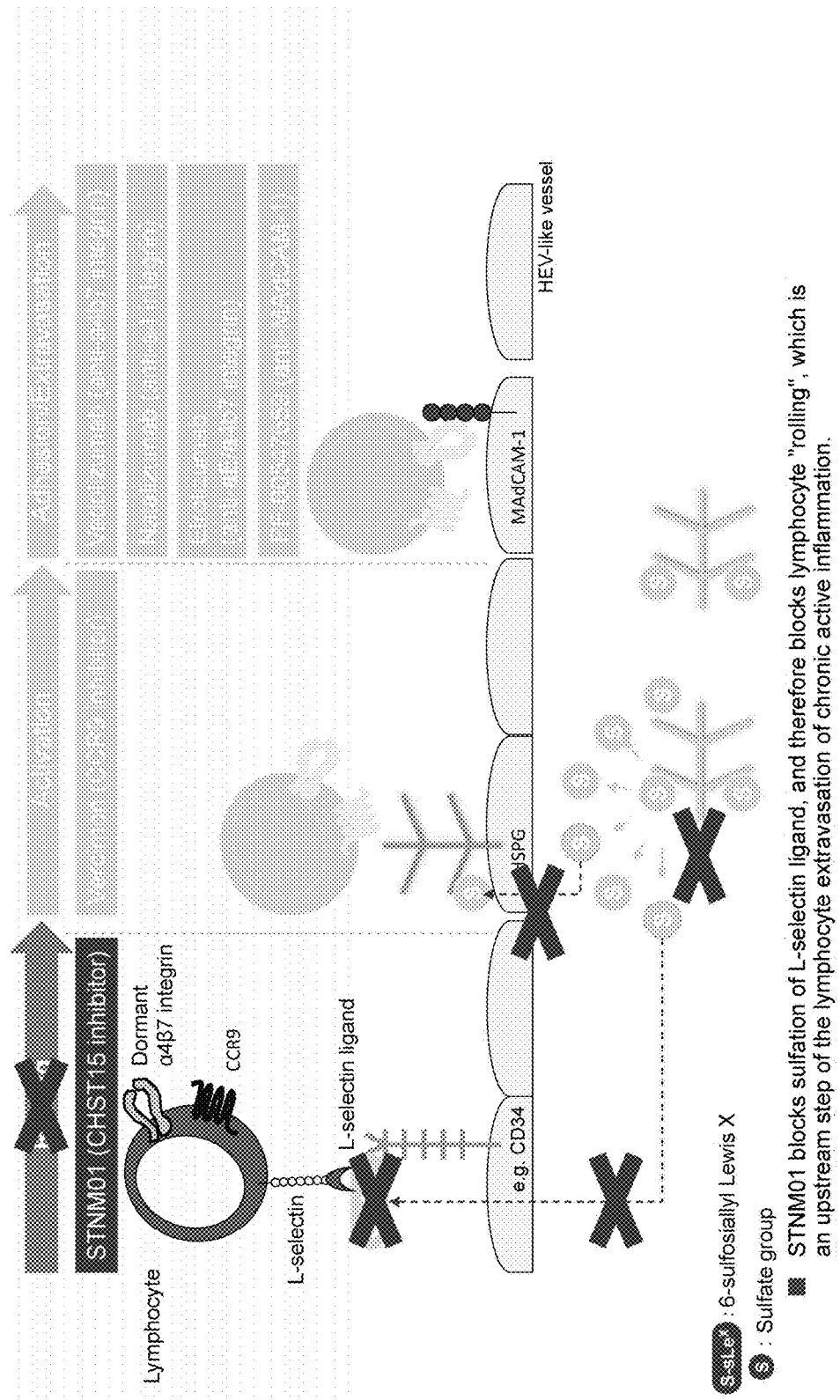
FIG. 6 is a schematic diagram indicating that the point of action of the pharmaceutical composition of the present invention is upstream from the point of action of existing therapeutic drugs for an inflammatory chronic disease.

The mechanism of action of existing therapeutic drugs of chronic inflammatory diseases is broadly divided into inhibition of the progression of invasion of lymphocytes into tissue and inhibition of an inflammatory reaction induced by invasion of tissue by lymphocytes. The mechanism of action of first-generation therapeutic drugs for the treatment of chronic inflammatory diseases (Infliximab, Adalimunab, Certolizumab pegol, Golimumab, Usteknumab and MED12070) consists of inhibition of TNF and cytokines involved in inflammatory reactions in tissue. In contrast, as shown in FIG. 5, second-generation therapeutic drugs for the treatment of chronic inflammatory diseases (Vercirnon, Vedolizumab, Natalizumab, Etrolizumab and PF-00547659) inhibit lymphocyte activation, strong adhesion of activated lymphocytes to vascular endothelial cells, and invasion into tissue from between vascular endothelial cells in the process of invasion of lymphocyte into tissue. Based on the results of analyzing the data of this clinical trial, the pharmaceutical composition of the present invention was clearly determined to lower sulfation of L-selectin ligand and decrease the invasion of lymphocyte in the tissue. As shown in FIG. 6, the pharmaceutical composition of the present invention inhibits rolling of lymphocytes within blood vessels by decreasing sulfation of L-selectin ligand during lymphocyte tissue invasion. This refers to the stage farthest upstream during the course of tissue invasion by lymphocytes. In other words, the point of action of the pharmaceutical composition of the present invention is farther upstream than the point of action of first-generation and second-generation therapeutic drugs for the treatment of chronic inflammatory diseases. Therefore, the pharmaceutical composition of the present invention was predicted to demonstrate a higher level of pharmacological efficacy than the concomitant use of first-generation and second-generation therapeutic drugs for the treatment of chronic inflammatory diseases.

Example 2

The present example provides an explanation of the results of a repeated-dose investigator initiated trial (IIT) in which biological preparation (Infliximab and/or Adalimunab)-resistant ulcerative colitis (UC) patients were administered the pharmaceutical composition of the present invention (STNM01).

Figure 7:
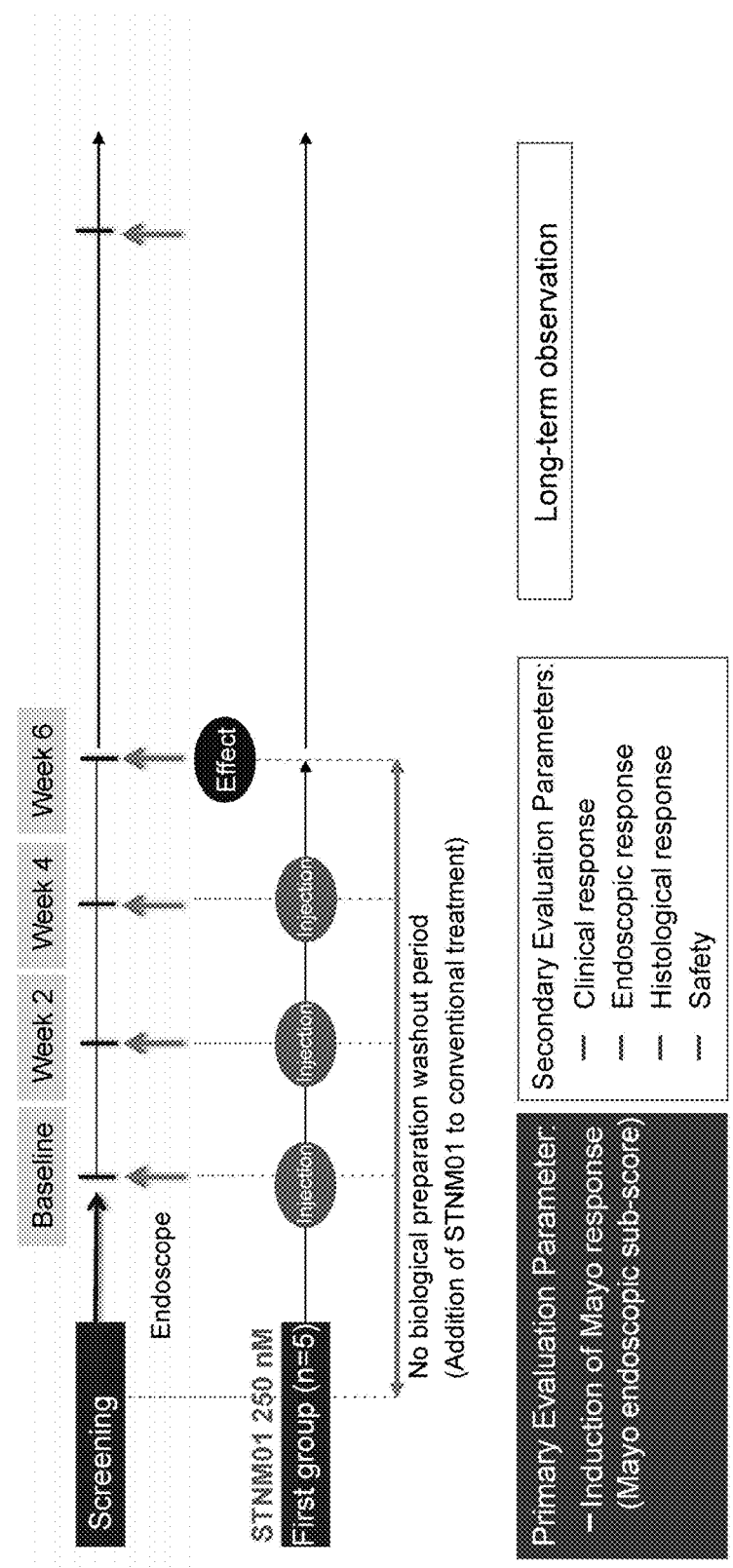
FIG. 7 is a schematic diagram explaining the study design of an investigator initiated trial on multiple repeated-dose administration of the pharmaceutical composition of the present invention.

FIG. 7 is a schematic diagram of the trial design of the investigator initiated trial of the present example. A total of five subjects observed to be resistant to a biological preparation (Infliximab and/or Adalimunab) in screening were administered 250 nM STNM01 by submucosal injection using an endoscope for a total of three times consisting of baseline (week 0) and in week 2 and week 4. In the trial of Example 1, subjects administered a biological preparation were administered STNM01 following a washout period during which time the biological preparation was not administered for one month. In the trial of Example 2, however, STNM01 was administered while continuing administration of the biological preparation. Evaluation parameters are the same as in the trial of Example 1.

Figure 8:
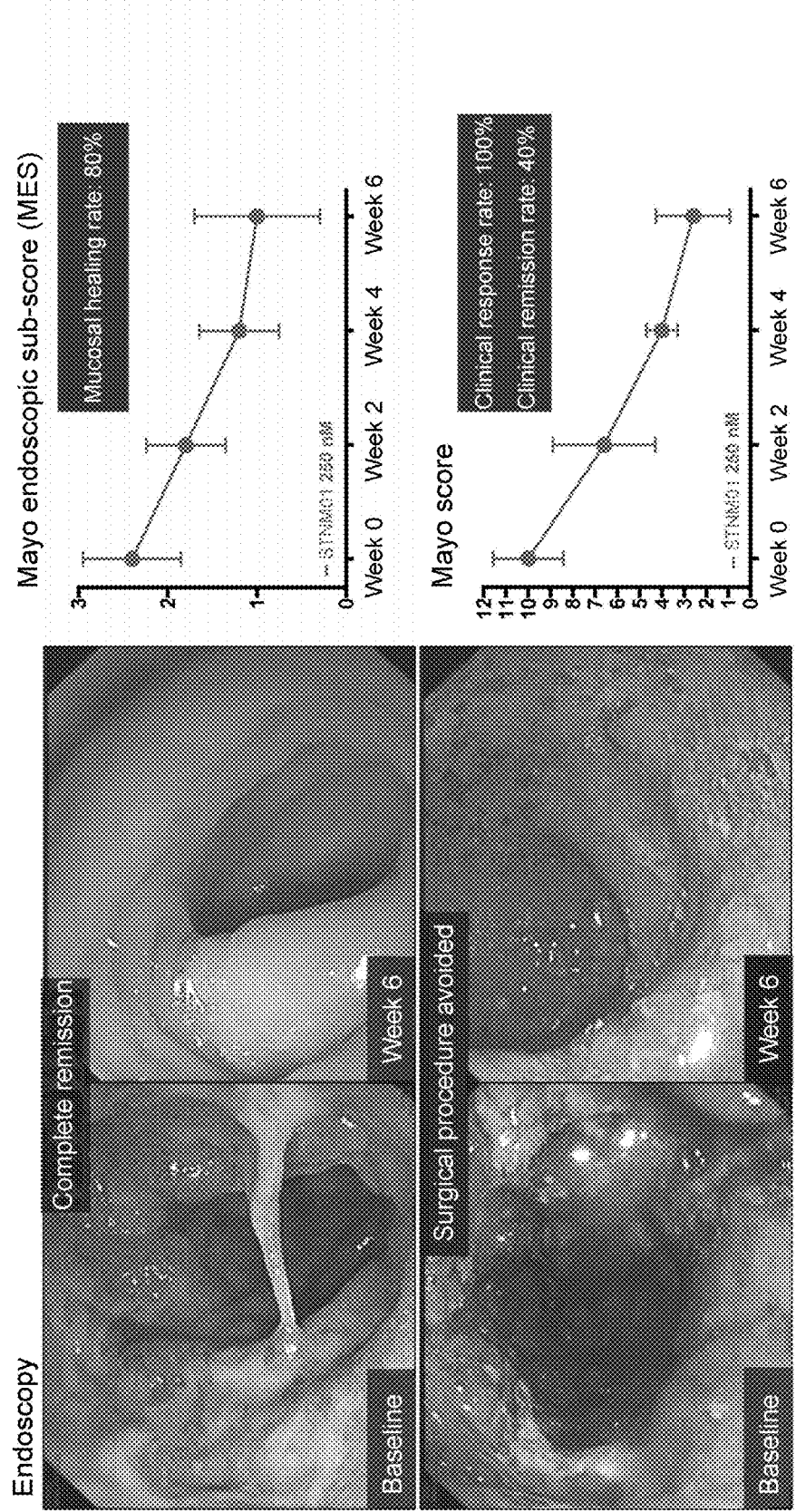
FIG. 8 depicts the results for the primary evaluation parameter (mucosal healing) and secondary evaluation parameter (systemic clinical response) of an investigator initiated trial on multiple repeated-dose administration of the pharmaceutical composition of the present invention.

FIG. 8 indicates highlights of results from the investigator initiated trial of the present example. The endoscopic photographs in the upper left corner of FIG. 8 indicate the affected area of the subject at baseline and in week 6 that had reached complete remission. Healing of the mucosa was observed in week 6. The endoscopic photographs in the lower left corner of FIG. 8 indicate the affected area of a seriously ill subject presenting with a large ulcer accompanied by bleeding at baseline and in week 6. Although this patient did not reach complete remission of the ulcer, surgery was able to be avoided according to comments made by the supervising physician. The upper right corner of FIG. 8 depicts a graph indicating time-based changes in Mayo endoscopic sub-scores (MES) of five subjects of the investigator initiated trial of the present example. Ultimately, the mucosal cure rate was 80%. The lower right corner of FIG. 8 depicts a graph indicating time-based changes in the Mayo scores of five subjects of the investigator initiated trial of the present example (Colombel, J. F., et al., Gastroenterology 2011: 141: 1194-1201). As shown in FIG. 8, improvement of systemic and local symptoms was observed as a result of repeated-dose administration of STNM01 to serious ulcerative colitis resistant to biological preparations. Ultimately, the clinical response rate was 100% and the clinical remission rate was 40%.

A summary of the results of other investigator initiated trials is as indicated below.

In terms of pathology, a reduction in inflammatory cell invasion and induction of an increase in goblet cells were observed. All five subjects progressed favorably without indicating clinical relapse for at least 8 months. Although one of the subjects exhibited intestinal bleeding in month 9 and another in month 11, the remaining three subjects entered remission after 9 months. In particular, although the one serious case was administered STNM01 in an imminent state as a final means immediately prior to surgery, since clinical effects appeared within two weeks, the status of the subject was monitored without performing surgery, and as a result, a surgical procedure was able to be avoided (according to comments by trial director). Although there were 3 of 5 refractory cases that were dependent on steroids, all three were able to maintain steroid-free remission for at least six months.

As has been described above, repeated-dose administration during a treatment introduction period of STNM01 of the present example demonstrated a rapid clinical response and effects that induced mucosal healing in refractory ulcerative colitis patients resistant to biological preparations, and what is more, that effect was indicated to be maintained over a span of more than six months (8 months or more in the present clinical trial) without having to add new systemically administered drugs.

On the basis of the examples, the pharmaceutical composition of the present invention was verified to demonstrate higher pharmacological efficacy than the concomitant use of biological preparations inhibiting invasion by leukocytes into tissue and/or biological preparations inhibiting inflammatory cytokines.

[Sequence Listing]

The invention claimed is:

1. A method for treating a chronic disease of a patient in need thereof, the method comprising: administrating a pharmaceutical composition in combination with a biological preparation that inhibits leukocyte tissue invasion, a biological preparation that inhibits inflammatory cytokines, or a combination thereof, to the patient, wherein the pharmaceutical composition comprises, as an active ingredient: (i) a siRNA that suppresses expression of CHST15 gene comprising a structure formed by hybridizing an RNA comprising the base sequence of SEQ ID NO: 1 with an RNA comprising the base sequence of SEQ ID NO: 2 complementary thereto, (ii) the siRNA of (i) having an overhang from an end thereof, or (iii) a DNA vector expressing the siRNA of (i) or (ii), wherein the biological preparation that inhibits leukocyte tissue invasion comprises at least one member selected from the group consisting of Etrolizumab, Vedolizumab, Natalizumab, PF-00547659 and Vercirnon, and the biological preparation that inhibits inflammatory cytokines comprises at least one member selected from the group consisting of an antibody that inhibits the inflammatory cytokines comprising TNF-a, IL-17, IL-18, IL-23, IL-1p and GM-CSF, an antibody fragment, or a specific binding partner for the inflammatory cytokines which is a single-domain antibody, and wherein the chronic disease is inflammatory bowel disease.

2. The method of claim 1, wherein the biological preparation that inhibits leukocyte tissue invasion is at least one member selected from the group consisting of Etrolizumab, Vedolizumab, Natalizumab, PF-00547659 and Vercirnon.

3. The method of claim 1, wherein the biological preparation that inhibits inflammatory cytokines inhibits a function of at least one molecule selected from the group consisting of TNF-α, IL-17 and IL-23.

4. The method of claim 1, wherein the administering is the pharmaceutical composition in combination with at least one of the biological preparations further comprises administering at least one member selected from the group consisting of a 5-aminosalicyclic acid preparation, a steroid preparation, a thiopurine preparation and an immunosuppressant.

5. The method of claim 4, wherein the immunosuppressant is tacrolimus or cyclosporine.

6. The method of claim 1, wherein the inflammatory bowel disease is Crohn's disease or ulcerative colitis.

7. The method of claim 1, wherein the administering comprises administering the pharmaceutical composition and at least one of the biological preparations systemically or locally.

8. The method of claim 7, wherein the chronic disease is a Crohn's disease or ulcerative colitis, and
the administering is a local administration, which is a submucosal administration into an intestine of the patient.

9. The method of claim 7, wherein the administration is a systemic administration, which is an oral administration, an intravenous injection or a combination thereof.

10. The method of claim 9, wherein the administering is an oral administration of a complex, the complex comprises an active ingredient and N-acetylated chitosan, and the active ingredient is: (i) the siRNA that suppresses the expression of CHST15 gene, or (ii) the siRNA of (i) having an overhang from an end thereof.

* * * * *

SEQUENCE LISTING

```
<160> NUMBER OF SEQ ID NOS: 6

<210> SEQ ID NO 1
<211> LENGTH: 25
<212> TYPE: RNA
<213> ORGANISM: Artificial Sequence
<220> FEATURE:
<223> OTHER INFORMATION: An artificially synthesized siRNA sequence

<400> SEQUENCE: 1
gauuguauuc aucuugcucu gcucc                                          25

<210> SEQ ID NO 2
<211> LENGTH: 25
<212> TYPE: RNA
<213> ORGANISM: Artificial Sequence
<220> FEATURE:
<223> OTHER INFORMATION: An artificially synthesized siRNA sequence

<400> SEQUENCE: 2
ggagcagagc aagaugaaua caauc                                          25

<210> SEQ ID NO 3
<211> LENGTH: 27
<212> TYPE: RNA
<213> ORGANISM: Artificial Sequence
<220> FEATURE:
<223> OTHER INFORMATION: An artificially synthesized siRNA sequence

<400> SEQUENCE: 3
gauuguauuc aucuugcucu gcuccau                                        27

<210> SEQ ID NO 4
<211> LENGTH: 27
<212> TYPE: RNA
<213> ORGANISM: Artificial Sequence
<220> FEATURE:
<223> OTHER INFORMATION: An artificially synthesized siRNA sequence

<400> SEQUENCE: 4
ggagcagagc aagaugaaua caaucag                                        27

<210> SEQ ID NO 5
<211> LENGTH: 4813
```

```
<212> TYPE: DNA
<213> ORGANISM: Homo sapiens
<220> FEATURE:
<221> NAME/KEY: CDS
<222> LOCATION: (614)..(2299)
<223> OTHER INFORMATION: NM_015892.4: Homo sapiens carbohydrate
      sulfotransferase 15 (CHST15), transcript variant 1, mRNA

<400> SEQUENCE: 5
```

| | |
|---|---:|
| gaggcggcgt gactcgggag ttgccggcgc ttcccggcgg tggcggcgtc tctggccggc | 60 |
| cttggtgcgg cgagccgagc gaggcagctc tgagccgcgc ggaaatctgg cattttttaa | 120 |
| agtttgcgcc ccacaaagag gaaatattcc aaaggtactc aggatgtaaa aggggagatc | 180 |
| ttcacagatg cctccgtgga tggcatggca atccatccat caatgagaag accatgattt | 240 |
| cttttaattt tctgtgtgtt tccacattcc ccagtgagaa ttcttccacc ttttttttgtg | 300 |
| ccatgggaaa aacctgaagg gcaggcagag ctgctcccga acttgtgacc ttctctgagg | 360 |
| ttgcagcggc tcttgtagaa catgactctg gacatcact tccttttgtt ttctttcgga | 420 |
| gctgaaccaa agaatgtgca ccctctttct ctagtgctgt ggtgtctgct tatttttgta | 480 |
| tttgtgcttt ccatccatct tctgtgatca caaggcattc ttaaggtttt ctagcacgac | 540 |
| ttgcggacat ccagactcgt gggggggccca cccatggctc ggtaagccag cagcccaggg | 600 |
| cactggcact acc atg agg cac tgc att aat tgc tgc ata cag ctg tta | 649 |
|                Met Arg His Cys Ile Asn Cys Cys Ile Gln Leu Leu | |
|                 1            5                 10 | |
| ccc gac ggc gca cac aag cag cag gtc aac tgc caa ggg ggc ccc cat | 697 |
| Pro Asp Gly Ala His Lys Gln Gln Val Asn Cys Gln Gly Gly Pro His | |
|               15                 20                 25 | |
| cac ggt cac cag gcg tgc ccc acg tgc aaa gga gaa aac aaa att ctg | 745 |
| His Gly His Gln Ala Cys Pro Thr Cys Lys Gly Glu Asn Lys Ile Leu | |
|         30                 35                 40 | |
| ttt cgt gtg gac agt aag cag atg aac ttg ctt gct gtt ctc gaa gtg | 793 |
| Phe Arg Val Asp Ser Lys Gln Met Asn Leu Leu Ala Val Leu Glu Val | |
| 45                 50                 55                 60 | |
| agg act gaa ggg aac gaa aac tgg ggt ggg ttt ttg cgc ttc aaa aag | 841 |
| Arg Thr Glu Gly Asn Glu Asn Trp Gly Gly Phe Leu Arg Phe Lys Lys | |
|                 65                 70                 75 | |
| ggg aag cga tgt agc ctc gtt ttt gga ctg ata ata atg acc ttg gta | 889 |
| Gly Lys Arg Cys Ser Leu Val Phe Gly Leu Ile Ile Met Thr Leu Val | |
|              80                 85                 90 | |
| atg gct tct tac atc ctt tct ggg gcc cac caa gag ctt ctg atc tca | 937 |
| Met Ala Ser Tyr Ile Leu Ser Gly Ala His Gln Glu Leu Leu Ile Ser | |
|                 95                100              105 | |
| tca cct ttc cat tac gga ggc ttc ccc agc aac ccc agc ttg atg gac | 985 |
| Ser Pro Phe His Tyr Gly Gly Phe Pro Ser Asn Pro Ser Leu Met Asp | |
|          110              115              120 | |
| agc gaa aac cca agt gac aca aag gag cat cac cac caa tcc tct gta | 1033 |
| Ser Glu Asn Pro Ser Asp Thr Lys Glu His His His Gln Ser Ser Val | |
| 125             130              135             140 | |
| aat aat att tca tac atg aag gac tat cca agc att aaa tta att atc | 1081 |
| Asn Asn Ile Ser Tyr Met Lys Asp Tyr Pro Ser Ile Lys Leu Ile Ile | |
|              145              150              155 | |
| aac agc atc aca act agg att gag ttc acg acc aga cag ctc cca gac | 1129 |
| Asn Ser Ile Thr Thr Arg Ile Glu Phe Thr Thr Arg Gln Leu Pro Asp | |
|            160              165              170 | |
| tta gaa gac ctt aag aag cag gag ttg cat atg ttt tca gtc atc ccc | 1177 |
| Leu Glu Asp Leu Lys Lys Gln Glu Leu His Met Phe Ser Val Ile Pro | |
| 175             180              185 | |

```
aac aaa ttc ctt cca aac agt aag agc ccc tgt tgg tac gag gag ttc      1225
Asn Lys Phe Leu Pro Asn Ser Lys Ser Pro Cys Trp Tyr Glu Glu Phe
    190             195                 200 tcg ggg cag aac acc acc gac ccc tac ctc acc aac tcc tac gtg ctc      1273
Ser Gly Gln Asn Thr Thr Asp Pro Tyr Leu Thr Asn Ser Tyr Val Leu
205                 210                 215                 220 tac tcc aag cgc ttc cgc tcc acc ttc gac gcc ctg cgc aag gcc ttc      1321
Tyr Ser Lys Arg Phe Arg Ser Thr Phe Asp Ala Leu Arg Lys Ala Phe
                    225                 230                 235 tgg ggc cac ctg gcg cac gcg cac ggg aag cac ttc cgc ctg cgc tgc      1369
Trp Gly His Leu Ala His Ala His Gly Lys His Phe Arg Leu Arg Cys
                240                 245                 250 ctg ccg cac ttc tac atc ata ggg cag ccc aag tgc ggg acc aca gac      1417
Leu Pro His Phe Tyr Ile Ile Gly Gln Pro Lys Cys Gly Thr Thr Asp
            255                 260                 265 ctc tat gac cgc ctg cgg ctg cac cct gag gtc aag ttc tcc gcc atc      1465
Leu Tyr Asp Arg Leu Arg Leu His Pro Glu Val Lys Phe Ser Ala Ile
        270                 275                 280 aag gag cca cac tgg tgg acc cgg aag cgc ttt gga atc gtc cgc cta      1513
Lys Glu Pro His Trp Trp Thr Arg Lys Arg Phe Gly Ile Val Arg Leu
285                 290                 295                 300 aga gat ggg ctg cga gac cgc tat ccc gtg gaa gat tat ctg gac ctc      1561
Arg Asp Gly Leu Arg Asp Arg Tyr Pro Val Glu Asp Tyr Leu Asp Leu
                    305                 310                 315 ttt gac ctg gcc gca cac cag atc cat caa gga ctg cag gcc agc tct      1609
Phe Asp Leu Ala Ala His Gln Ile His Gln Gly Leu Gln Ala Ser Ser
                320                 325                 330 gca aag gag cag agc aag atg aat aca atc att atc ggg gag gcc agt      1657
Ala Lys Glu Gln Ser Lys Met Asn Thr Ile Ile Ile Gly Glu Ala Ser
            335                 340                 345 gcc tcc acg atg tgg gat aat aat gcc tgg acg ttc ttc tac gac aac      1705
Ala Ser Thr Met Trp Asp Asn Asn Ala Trp Thr Phe Phe Tyr Asp Asn
        350                 355                 360 agc acg gat ggc gag cca ccg ttt ctg acg cag gac ttc atc cac gcc      1753
Ser Thr Asp Gly Glu Pro Pro Phe Leu Thr Gln Asp Phe Ile His Ala
365                 370                 375                 380 ttt cag cca aat gcc aga ctg att gtc atg ctc agg gac cct gtg gag      1801
Phe Gln Pro Asn Ala Arg Leu Ile Val Met Leu Arg Asp Pro Val Glu
                    385                 390                 395 agg ttg tac tca gac tat ctc tac ttt gca agt tcg aat aaa tcc gcg      1849
Arg Leu Tyr Ser Asp Tyr Leu Tyr Phe Ala Ser Ser Asn Lys Ser Ala
                400                 405                 410 gac gac ttc cat gag aaa gtg aca gaa gca ctg cag ctg ttt gaa aat      1897
Asp Asp Phe His Glu Lys Val Thr Glu Ala Leu Gln Leu Phe Glu Asn
            415                 420                 425 tgc atg ctt gat tat tca ctg cgc gcc tgc gtc tac aac aac acc ctc      1945
Cys Met Leu Asp Tyr Ser Leu Arg Ala Cys Val Tyr Asn Asn Thr Leu
        430                 435                 440 aac aac gcc atg cct gtg agg ctc cag gtt ggg ctc tat gct gtg tac      1993
Asn Asn Ala Met Pro Val Arg Leu Gln Val Gly Leu Tyr Ala Val Tyr
445                 450                 455                 460 ctt ctg gac tgg ctc agc gtt ttt gac aag caa cag ttt ctc att ctt      2041
Leu Leu Asp Trp Leu Ser Val Phe Asp Lys Gln Gln Phe Leu Ile Leu
                    465                 470                 475 cgc ctg gaa gat cat gca tcc aac gtc aag tac acc atg cac aag gtc      2089
Arg Leu Glu Asp His Ala Ser Asn Val Lys Tyr Thr Met His Lys Val
                480                 485                 490
```

```
ttc cag ttt ctg aac cta ggg ccc tta agt gag aag cag gag gct ttg    2137
Phe Gln Phe Leu Asn Leu Gly Pro Leu Ser Glu Lys Gln Glu Ala Leu
            495                 500                 505 atg acc aag agc ccc gca tcc aat gca cgg cgt ccc gag gac cgg aac    2185
Met Thr Lys Ser Pro Ala Ser Asn Ala Arg Arg Pro Glu Asp Arg Asn
510                 515                 520 ctg ggg ccc atg tgg ccc atc aca cag aag att ctg cgg gat ttc tac    2233
Leu Gly Pro Met Trp Pro Ile Thr Gln Lys Ile Leu Arg Asp Phe Tyr
525                 530                 535                 540 agg ccc ttc aac gct agg ctg gcg cag gtc ctc gcg gat gag gcg ttt    2281
Arg Pro Phe Asn Ala Arg Leu Ala Gln Val Leu Ala Asp Glu Ala Phe
            545                 550                 555 gcg tgg aag acg acg tga gagctgaatt gttgctgcac gtgctgggcc           2329
Ala Trp Lys Thr Thr
            560 cgccaatgcc gtcatcatca ggattttaca aatctctttg cggggaactg tttcactcat    2389
ggtatggaaa accccaggac tctgccactc taggcacaca tgaattataa ccattttgga    2449
atttccttcg tgatgttcga gagctcagca atggacccct cacagagctc ctctatccga    2509
ggccattgga gaccccagtt tctcaagaat tcagctctgc tctgagcgtc ctggagcttg    2569
gggatgcagc cagctggcct gcactgggtg tggagagaac cctagggaa ggcagcctgg     2629
ccctgcccgc ctccgccttc tggagagcct ctgggttctg agtcagcaag ccagaggtca    2689
tgccacaggc ctggctggaa cttacacttc acgttccctt ttttttcccc tagagatggg    2749
gtctcgccgt gttgcacaga ctgtctgtat tcaatggcta tcttcacagg tgtgatcata    2809
ccacattcac ttctgaaaca ctcttgttgc gatcgctaac ctcactggga cagagaaccg    2869
cagtctttcg agaatggagg ctcttcattt tttttttctc ctttactcca aactcagccc    2929
tccagtttct tcagatgtaa accctgttaa cgtcactgtt tccaaaagga aaaaaataag    2989
tcagttttg gcagcacctt catctttctg acctcctcct attctgtcct tgtggactta    3049
tgtttaacat agaaaatgaa tgcgtttaaa acaaaaccac tttctgcatt taaccagtcc    3109
tggctctctc tctgctgcct cttcatacgt tttctcaaga acttcagttt ataattggaa    3169
gagaaatttt tgctgttaat gccagaatga gcaacctcaa ggaattgaac acttcttgga    3229
aaatctaggt aattcaagcc ctcatcaggt ttacaagatc atcagagaaa cagaggattt    3289
taattttag ttctggccgg ctacaggctc catttctctg ccttcccatt ggaaatagtt     3349
tatttccaca ttctccactg cgtgtggtca agttcctca cccagcaagg gactatagat     3409
actcgtgtcc caattccaaa acacaatgca caagctgaac ttgggctgaa cgtggcgtgt    3469
tgagatttgg aatgaggttt ctaagagccg tgttcttcat ggaattttcc aggccacttg    3529
gcagcttggt ttaccgatgg atgggctaga gatcttgtcg tttcttggaa gtcacaggga    3589
agattgaaga gaacgcttga gcatccttgg caacagccca ggtgggacct ggatgaagct    3649
ttgcactcaa gtattgtcaa gggaagcttc ctgtgaacca agttctcag gccaaggtct     3709
cgcccaccaa agccagaaag tgcaagcacc cgtctaccca gctctaactt gtatgtgtga    3769
gacagaccag gcttcggggg taggaggatc tgcagttgtt cagccgtctt tctgctggtg    3829
ttgtctttct gccatcagag aagggacaca cagcccgttc gaaggtgtgc agagggctct    3889
gagcgccagg atggccaggg ctgttttgc tactgaagga gcgtgtgtcc tgaactccca     3949
cttgcaggga cagtccccac cttctctata gccggcactg ggagcagccg ccagcaggga    4009
aatctggcct gagcacaagg atgctttagg gagagatcac ttcagtgtgt gtgtatattt    4069
```

-continued

```
atttgcagta cagtgcgcgc gtgtgtgtgt gtgtacgcgc acgtgtgggt gagtgcgtct    4129
tctgagtggg ttctgttcag ttgctaatga ggctcctccg ctctggacac aacccttttta   4189 tagattaatt tctctgccaa ttaacttgtc attttcagta catatttac tattccacac     4249 caaccataat tacaacaagg gattttctt atgcactcct atgcatgtga ataacatgtg     4309
gtgtaattct gcttcttaca gaagtattac tgaaggtatt atttccaata ttatttggtt    4369
tattatgcgg atcttttta tatatgcagt cccatccctt ctgtgccact caatgccatc     4429
cagacatggt tttcctcc aggggccttt ctctccagag ggcacttcgg ctgcctctgc      4489
ttcctctcat tcgaggcccg gctcttgctg acagaatagg ttccgttctg ggcggtggtt    4549
ctcgagcctg ccattcaaaa ccaaagcaaa ttggagcatt tctcacaaca tggtattgaa    4609
gttccttttt gttctcaaaa gttgtgaccg tgttaaattg tactcccta gtcctgtaag     4669 gtatgttaag tgaatcgcag ttacgctgta cttttattaa tatttaacat aattaaagat    4729
ggacccataa gagtgacgcc tgtggagcgc gtgctcttcc tctgcagcca agcaaaaaaa    4789
aaaaaaaaaa aaaaaaaaaa aaaa                                           4813
```

<210> SEQ ID NO 6
<211> LENGTH: 561
<212> TYPE: PRT
<213> ORGANISM: Homo sapiens

<400> SEQUENCE: 6

```
Met Arg His Cys Ile Asn Cys Cys Ile Gln Leu Leu Pro Asp Gly Ala
1               5                   10                  15

His Lys Gln Gln Val Asn Cys Gln Gly Gly Pro His Gly His Gln
            20                  25                  30

Ala Cys Pro Thr Cys Lys Gly Glu Asn Lys Ile Leu Phe Arg Val Asp
        35                  40                  45

Ser Lys Gln Met Asn Leu Leu Ala Val Leu Glu Val Arg Thr Glu Gly
    50                  55                  60

Asn Glu Asn Trp Gly Gly Phe Leu Arg Phe Lys Lys Gly Lys Arg Cys
65                  70                  75                  80

Ser Leu Val Phe Gly Leu Ile Ile Met Thr Leu Val Met Ala Ser Tyr
                85                  90                  95

Ile Leu Ser Gly Ala His Gln Glu Leu Leu Ile Ser Ser Pro Phe His
            100                 105                 110

Tyr Gly Gly Phe Pro Ser Asn Pro Ser Leu Met Asp Ser Glu Asn Pro
        115                 120                 125

Ser Asp Thr Lys Glu His His His Gln Ser Ser Val Asn Asn Ile Ser
    130                 135                 140

Tyr Met Lys Asp Tyr Pro Ser Ile Lys Leu Ile Ile Asn Ser Ile Thr
145                 150                 155                 160

Thr Arg Ile Glu Phe Thr Thr Arg Gln Leu Pro Asp Leu Glu Asp Leu
                165                 170                 175

Lys Lys Gln Glu Leu His Met Phe Ser Val Ile Pro Asn Lys Phe Leu
            180                 185                 190

Pro Asn Ser Lys Ser Pro Cys Trp Tyr Glu Glu Phe Ser Gly Gln Asn
        195                 200                 205

Thr Thr Asp Pro Tyr Leu Thr Asn Ser Tyr Val Leu Tyr Ser Lys Arg
    210                 215                 220

Phe Arg Ser Thr Phe Asp Ala Leu Arg Lys Ala Phe Trp Gly His Leu
225                 230                 235                 240
```

```
Ala His Ala His Gly Lys His Phe Arg Leu Arg Cys Leu Pro His Phe
            245                 250                 255
Tyr Ile Ile Gly Gln Pro Lys Cys Gly Thr Thr Asp Leu Tyr Asp Arg
            260                 265                 270
Leu Arg Leu His Pro Glu Val Lys Phe Ser Ala Ile Lys Glu Pro His
        275                 280                 285
Trp Trp Thr Arg Lys Arg Phe Gly Ile Val Arg Leu Arg Asp Gly Leu
    290                 295                 300
Arg Asp Arg Tyr Pro Val Glu Asp Tyr Leu Asp Leu Phe Asp Leu Ala
305                 310                 315                 320
Ala His Gln Ile His Gln Gly Leu Gln Ala Ser Ser Ala Lys Glu Gln
                325                 330                 335
Ser Lys Met Asn Thr Ile Ile Ile Gly Glu Ala Ser Ala Ser Thr Met
            340                 345                 350
Trp Asp Asn Asn Ala Trp Thr Phe Phe Tyr Asp Asn Ser Thr Asp Gly
        355                 360                 365
Glu Pro Pro Phe Leu Thr Gln Asp Phe Ile His Ala Phe Gln Pro Asn
    370                 375                 380
Ala Arg Leu Ile Val Met Leu Arg Asp Pro Val Glu Arg Leu Tyr Ser
385                 390                 395                 400
Asp Tyr Leu Tyr Phe Ala Ser Ser Asn Lys Ser Ala Asp Asp Phe His
                405                 410                 415
Glu Lys Val Thr Glu Ala Leu Gln Leu Phe Glu Asn Cys Met Leu Asp
            420                 425                 430
Tyr Ser Leu Arg Ala Cys Val Tyr Asn Asn Thr Leu Asn Asn Ala Met
        435                 440                 445
Pro Val Arg Leu Gln Val Gly Leu Tyr Ala Val Tyr Leu Leu Asp Trp
    450                 455                 460
Leu Ser Val Phe Asp Lys Gln Gln Phe Leu Ile Leu Arg Leu Glu Asp
465                 470                 475                 480
His Ala Ser Asn Val Lys Tyr Thr Met His Lys Val Phe Gln Phe Leu
                485                 490                 495
Asn Leu Gly Pro Leu Ser Glu Lys Gln Glu Ala Leu Met Thr Lys Ser
            500                 505                 510
Pro Ala Ser Asn Ala Arg Arg Pro Glu Asp Arg Asn Leu Gly Pro Met
        515                 520                 525
Trp Pro Ile Thr Gln Lys Ile Leu Arg Asp Phe Tyr Arg Pro Phe Asn
    530                 535                 540
Ala Arg Leu Ala Gln Val Leu Ala Asp Glu Ala Phe Ala Trp Lys Thr
545                 550                 555                 560
Thr
```